United States Patent
Parker et al.

(10) Patent No.: US 11,199,557 B2
(45) Date of Patent: Dec. 14, 2021

(54) REMOTE TESTING OF LABORATORY INSTRUMENTS

(71) Applicant: Beckman Coulter, Inc., Brea, CA (US)

(72) Inventors: Caren E. Parker, Orlando, FL (US); Craig R. Cole, East Garrison, CA (US); Sadasiva R. Guntupalli, Irvine, CA (US)

(73) Assignee: Beckman Coulter, Inc., Brea, CA (US)

( * ) Notice: Subject to any disclaimer, the term of this patent is extended or adjusted under 35 U.S.C. 154(b) by 354 days.

(21) Appl. No.: 16/396,186

(22) Filed: Apr. 26, 2019

(65) Prior Publication Data

US 2019/0252072 A1 Aug. 15, 2019

Related U.S. Application Data

(63) Continuation of application No. PCT/US2017/058467, filed on Oct. 26, 2017.
(Continued)

(51) Int. Cl.
*G16H 40/67* (2018.01)
*G01N 35/00* (2006.01)
(Continued)

(52) U.S. Cl.
CPC ............ *G01N 35/00871* (2013.01); *G01N 35/0092* (2013.01); *G06Q 10/06* (2013.01); *G06Q 10/06314* (2013.01); *G06Q 10/103* (2013.01); *G06Q 50/00* (2013.01); *G16H 10/40* (2018.01); *G16H 40/67* (2018.01)

(58) Field of Classification Search
CPC .......... G16H 40/67; G16H 10/40; G01N 35/00871; G01N 35/0092; G06Q 10/06314; G06Q 10/103; G06Q 50/00; G06Q 10/06
See application file for complete search history.

(56) References Cited

U.S. PATENT DOCUMENTS 5,946,471 A * 8/1999 Voorhees ........... G01R 19/2516
703/23
6,192,320 B1 * 2/2001 Margrey ............ G01N 35/00871
702/84
(Continued)

FOREIGN PATENT DOCUMENTS

CN 1530817 A 9/2004
CN 101926156 B 12/2010
(Continued)

OTHER PUBLICATIONS

Miguel A. Muñoz, Context-Aware Mobile Communication in Hospitals, 9 pages, 2003 (Year: 2003).*
(Continued)

*Primary Examiner* — Tung S Lau
(74) *Attorney, Agent, or Firm* — Frost Brown Todd LLC

(57) ABSTRACT

Experimental studies can be conducted in an environment where one or more laboratories communicate with a network instrument monitoring center over a network. In such an environment, an individual at the network instrument monitoring center can be enabled to simultaneously oversee studies at multiple remote laboratories, rather than requiring dedicated individuals at each of the laboratories to oversee the studies at their respective labs.

10 Claims, 20 Drawing Sheets

Related U.S. Application Data

(60) Provisional application No. 62/413,115, filed on Oct. 26, 2016.

(51) Int. Cl.
| | |
|---|---|
| *G16H 10/40* | (2018.01) |
| *G06Q 50/00* | (2012.01) |
| *G06Q 10/06* | (2012.01) |
| *G06Q 10/10* | (2012.01) |

(56) References Cited

U.S. PATENT DOCUMENTS

| | | | |
|---|---|---|---|
| 7,661,013 B2 | 2/2010 | Berman et al. | |
| 7,680,605 B2 | 3/2010 | Yung et al. | |
| 7,761,809 B2 | 7/2010 | Bukovec | |
| 8,230,041 B2 | 7/2012 | Minowa et al. | |
| 8,626,149 B2 | 1/2014 | Steenstra et al. | |
| 9,407,861 B2 | 8/2016 | Huenerfauth et al. | |
| 9,443,710 B2 | 9/2016 | Platt et al. | |
| 9,842,295 B2 | 12/2017 | Fisher | |
| 9,935,852 B2 | 4/2018 | Nasgowitz et al. | |
| 9,952,659 B2 | 4/2018 | Joseph et al. | |
| 10,197,993 B2 | 2/2019 | Lesher | |
| 10,431,335 B2 | 10/2019 | Cork et al. | |
| 10,739,362 B2* | 8/2020 | Goemann-Thoss | G01N 33/68 |
| 2004/0034478 A1* | 2/2004 | Yung | G05B 15/02 |
| | | | 702/19 |
| 2004/0042471 A1* | 3/2004 | Yung | G05B 15/02 |
| | | | 370/401 |
| 2004/0130572 A1 | 7/2004 | Bala | |
| 2005/0038676 A1* | 2/2005 | Showalter | G16H 10/40 |
| | | | 705/2 |
| 2005/0106736 A1* | 5/2005 | Yung | G16H 40/63 |
| | | | 436/43 |
| 2005/0143956 A1 | 6/2005 | Long et al. | |
| 2006/0074597 A1 | 4/2006 | Raphael et al. | |
| 2006/0206358 A1 | 9/2006 | Beaver | |
| 2007/0129894 A1* | 6/2007 | Yung | G05B 23/0264 |
| | | | 702/19 |
| 2007/0196909 A1* | 8/2007 | Showalter | G06Q 10/00 |
| | | | 435/283.1 |
| 2009/0313347 A1* | 12/2009 | Engel | G06F 15/16 |
| | | | 709/212 |
| 2010/0229022 A1 | 9/2010 | Anand et al. | |
| 2011/0245089 A1 | 10/2011 | Scott et al. | |
| 2012/0041777 A1 | 2/2012 | Case et al. | |
| 2012/0290104 A1 | 5/2012 | Holt et al. | |
| 2013/0014012 A1 | 1/2013 | Boucher et al. | |
| 2014/0184223 A1 | 7/2014 | Otvos et al. | |
| 2014/0282181 A1 | 9/2014 | Declerck | |
| 2015/0127270 A1* | 5/2015 | Goemann-Thoss | G01N 33/48 |
| | | | 702/31 |
| 2016/0018347 A1 | 1/2016 | Drbal et al. | |
| 2016/0292393 A1* | 10/2016 | Balwani | G16H 10/40 |
| 2017/0017538 A1 | 1/2017 | Rudorfer et al. | |
| 2019/0146466 A1 | 5/2019 | Lesher | |
| 2020/0185091 A1 | 6/2020 | Davis | |

FOREIGN PATENT DOCUMENTS

| | | | |
|---|---|---|---|
| CN | 102867013 A | 1/2013 | |
| CN | 107271650 A | 10/2017 | |
| CN | 109314650 A | 2/2019 | |
| EP | 1437648 A2 | 1/2006 | |
| EP | 1779317 A1 * | 5/2007 | G06Q 50/00 |
| EP | 2243285 A1 | 10/2010 | |
| EP | 2544131 A1 | 1/2013 | |
| EP | 2756294 A1 | 7/2014 | |
| EP | 2778994 A1 | 9/2014 | |
| EP | 3140761 A1 | 3/2017 | |
| EP | 3226002 A1 | 10/2017 | |
| EP | 3033594 A1 | 3/2018 | |
| EP | 3465984 A1 | 4/2019 | |
| EP | 3533065 A1 | 9/2019 | |
| JP | 2004-213677 | 2/2007 | |
| JP | 2017-187473 | 10/2017 | |
| WO | WO 2003/010612 A2 * | 2/2003 | G05B 19/042 |
| WO | WO 2007/087136 A2 | 8/2007 | |
| WO | WO 2009/079558 A1 | 6/2009 | |
| WO | WO 2011/067559 A1 | 6/2011 | |
| WO | WO 2013/039772 A1 | 3/2013 | |
| WO | WO 2015/023443 A1 | 2/2015 | |
| WO | WO 2015/171581 A1 | 11/2015 | |
| WO | WO 2015/179370 A1 | 11/2015 | |
| WO | WO 2017/214030 A1 | 12/2017 | |
| WO | WO 2019/216975 A1 | 11/2019 | |

OTHER PUBLICATIONS

International Search Report and Written Opinion dated Jan. 30, 2018 for Application No. PCT/US2017/058467, 11 pgs.

International Search Report and Written Opinion dated Jul. 30, 2020 for International Application No. PCT/US2020/014702, 35 pages.

Examination Report dated Jun. 29, 2021 for Indian Patent Application No. 201947012118, 5 pages.

Office Action dated Jul. 16, 2021 for European Patent Application No. 17798039.8, 8 pages.

\* cited by examiner

| Test Name | Test ID | Enabled | Default Sample Type | Default Units | Decimal Places | Revision | Pipettor |
|---|---|---|---|---|---|---|---|
| FT3 | 212 | ✓ | Serum | pg/mL | 1 | 3 | 0.2 |
| PTH | 214 | ✓ | Serum | pg/mL | 0 | 3 | 0.2 |
| FRT4 | 226 | ✓ | Serum | ng/dL | 2 | 2 | 0.2 |
| BNP2 | 261 | ✓ | Serum | pg/mL | 1 | 2 | 0.2 |
| VitD | 271 | ✓ | Serum | ng/mL | 2 | 1 | 0.2 |
| HCG5 | 273 | ✓ | Serum | mIU/mL | 2 | 1 | 0.2 |
| TnIx | 268 | ✓ | Serum | pg/mL | 3 | 1 | 0.2 |
| dBNP2 | 1261 | ✓ | Serum | pg/mL | 1 | 1 | 0.2 |
| B-CG5 | 1273 | ✓ | Serum | mIU/mL | 0 | 1 | 0.2 |

Define/Edit User-Defined Chemistry

| Number | Chem | | | |
|---|---|---|---|---|
| 3 | OXYX | | | Page 2 of 3 |

| Processing Parameters | First Inject | Second Inject | Third Inject |
|---|---|---|---|
| Component | A | None | B |
| Dispense Volume | 200 uL | uL | 50 uL |
| Inject Time | | -180 sec | 48 sec |
| Sample Volume | 15 uL | | |

| Reagent | Blank | Initial | Reaction 1 | Reaction 2 |
|---|---|---|---|---|
| Start Read | -83 sec | 96 sec | 96 sec | sec |
| End Read | -20 sec | 144 sec | 144 sec | sec |

[Restore F1] [UDR + F3] [Cancel F9] [Done F10]

---

| 3 | OXYX | Page 1 of 3 |
|---|---|---|

Chemistry Parameters

| Reaction Type | Rate 1 | Calculation Factor | 1000.000 |
|---|---|---|---|
| Units | mA/min | No. of Calibrators | 3 |
| Precision | XX | Setpoints 1 | 0.000 | 4 | |
| Reaction Direction | Positive | 2 | 300.000 | 5 | |
| Math Model | DAT | 3 | 1000.000 | 6 | |
| Primary Wavelength | 340 | Cal Time Limit | 336 hours |
| Secondary Wavelength | 650 | | |

[Restore F1] [UDR + F3] [Cancel F9] [Done F10]

---

| 3 | OXYX | | | Page 3 of 3 |
|---|---|---|---|---|

| Error Detection Limits | Blank | Reaction 1 | Reaction 2 |
|---|---|---|---|
| ABS Low Limit | -1.500 | -1.500 | -1.500 |
| ABS High Limit | 2.200 | 2.200 | 2.200 |
| Rate Low Limit | -1.500 | -1.500 | -1.500 |
| Rate High Limit | 2.200 | 2.200 | 2.200 |
| Mean Deviation | 2.200 | 2.200 | 2.200 |

| Substrate Depletion | | Multipoint Span | | | Usable Result Range | |
|---|---|---|---|---|---|---|
| Initial Rate | 99.999 | 1-2 | 0.000 | 2-3 | 0.000 | 3-1 | 0.000 | Low Limit | 0.000 |
| Delta ABS | 2.200 | | | | | High Limit | 99999.999 |

[Restore F1] [UDR + F3] [Cancel F9] [Done F10]

FIG. 5C

Program Sample

Sample Status: Not Programmed

Rack [ ]  Pos [ ]  ☐ STAT  Sample Type: Serum ▽  Patient ID [ ]
601 —
Sample ID [ ]  Sample Comment [ ] ▽  Patient Name [ ]

Panel No(s) [ ]  Panels  Chem No(s) [ ]

| ☐ NA¹ | ☐ K² | ☐ CL³ | ☐ CO2⁴ | ☐ CALC⁵ | ☐ ALBm⁶ | ☐ BUNm⁷ | ☐ CREm⁸ | ☐ GLUCm⁹ |
| ☐ PHOSm¹⁰ | ☐ TPm¹¹ | ☐ A1c¹² | ☐ A1c2¹³ | ☐ ACTM¹⁴ | ☐ ALB¹⁵ | ☐ ALP¹⁶ | ☐ ALT¹⁷ | ☐ ALT-¹⁸ |
| ☐ AMM¹⁹ | ☐ AMPH²⁰ | ☐ AMY²¹ | ☐ AMYZ²² | ☐ AppA²³ | ☐ ApoB²⁴ | ☐ ASO-²⁵ | ☐ AST²⁶ | ☐ AST-²⁷ |
| ☐ BARB²⁸ | ☐ BENZ²⁹ | ☐ BNZG³⁰ | ☐ BUN³¹ | ☐ C3³² | ☐ C4³³ | ☐ CAR³⁴ | ☐ CCWA³⁵ | ☐ CHE³⁶ |
| ☐ CHOL³⁷ | ☐ CK³⁸ | ☐ CK-³⁹ | ☐ CKMB⁴⁰ | ☐ COCM⁴¹ | ☐ CO2E⁴² | ☐ CREA⁴³ | ☐ CRP⁴⁴ | ☐ C-RP⁴⁵ |

| Demog F2 | Options F3 | Batch F4 | Control F5 | Rerun F6 | Clear F7 | Racks F8 | List F9 | Next F10 |

Sample Options

System Replicates [1]  ☐ Serum Index
Sample Replicates [ ]  Off-Line Dilution Factor [ I ]

| Chem | Manual ORDAC | Reps | Chem | Manual ORDAC | Reps | Chem | Manual ORDAC | Reps |
|---|---|---|---|---|---|---|---|---|
| CL | | 5 | CO2 | | 5 | | | |
| | | | | | | | | |
| | | | | | | | | |
| | | | | | | | | |
| | | | | | | | | |
| | | | | | | | | |
| | | | | | | | | |

OK   Cancel

Program Batch

| | Reps | Pos | Sample IDs | | Reps | Pos | Sample IDs |
|---|---|---|---|---|---|---|---|
| 1 | 101 | 1 | QC11 | 2 | 101 | 2 | QC12 |
| 3 | 101 | 3 | QC13 | 4 | 101 | 4 | QC14 |
| 5 | | | | 6 | | | |
| 7 | | | | 8 | | | |
| 9 | | | | 10 | | | |
| 11 | | | | 12 | | | |
| 13 | | | | 14 | | | |
| 15 | | | | 16 | | | |
| 17 | | | | 18 | | | |
| 19 | | | | 20 | | | |

Rack   End

FIG. 6

Reagent Order - Instrument  Date: _____

| Account Name: | Contact: |
|---|---|
| Address: | Phone: |
| City, State: | Email: |

| ASC: |
|---|
| CEC: |
| IPM: |

*Please indicate menu for the new instrumentation - "1" indicates YES*

| Anemia Assays | Skeletal | Immuno Controls |
|---|---|---|
| ☐ EPO | ☐ GH | (Control kits will automatically ship with corresponding menu) |
| ☐ Ferritin | ☐ Ostase | |
| ☐ Folate | ☐ PTH, Intact | 5 Order additional kits |
| ☐ Folate, RBC | ☐ PTH, Interoperative | Only as needed |
| ☐ Intrinsic Factor | Specialty | ☐ IL - 6 Control |
| ☐ sTransferin Receptor | ☐ Cortisol | ☐ Inhibin A QC |
| ☐ Vit B12 | ☐ IgE | ☐ Intrinsic Factor Control |
| Cardiovascular | ☐ Insulin | ☐ Ostase Control |
| ☐ AccuTnI+3 | ☐ IL-6 (RUO) | ☐ PAPP-A Control |
| ☐ CKMB | ☐ Vitamin D | ☐ Rubella IgG Control |
| ☐ Digoxin | Thyroid | ☐ SHBG Control |
| ☐ Myoglobin | ☐ FT3 | ☐ sTfR Control |
| Infectious Disease | ☐ FT4 | ☐ Toxo IgG Control |
| ☐ Rubella IgG | ☐ TT3 | ☐ Toxo IgM - II Controll |
| ☐ ToxoIgG | ☐ TT4 | Request as needed: |
| ☐ Toxo IgG II | ☐ TSH | ☐ CEA Control |
| Reproductive | ☐ TSH, Fast | ☐ PSA Control |
| ☐ BhCG, Total (5th IS) | ☐ T-Iptake | ☐ PSA, Free-PSA Control |
| ☐ DHEA-S | ☐ Tg | ☐ Biorad Maternal QC for bHCG |
| ☐ Estradiol | ☐ TgAb II | |
| ☐ Estriol, Unc | ☐ TPO-Ab | 4 Is the customer a current Immuno customer? |
| ☐ FSH | Tumor | |
| ☐ Inhibin A | ☐ AFP | ☐ Yes |
| ☐ LH | ☐ BR monitor (for 15-3) | ☐ No |
| ☐ PAPP-A (RUO) | ☐ CEA | |
| ☐ Progesterone | ☐ GI Monitor (for 19-9) | Enter value of "1" in |
| ☐ Prolactin | ☐ OV Monitor (for 125) | appropriate box |
| ☐ SHBG | ☐ PSA | |
| ☐ Testosterone | ☐ Free-PSA | |

| General Menu | TDM's | Protein/Serology | Esoteric Controls |
|---|---|---|---|
| ☐ ALP | ☐ THE | ☐ IGA | (One kit will automatically ship with corresponding menu) |
| ☐ ALT | ☐ TOB | ☐ IGG | |
| ☐ AMY G7 | ☐ VANC | ☐ IGM | 4 Order additional kits |
| ☐ AST | ☐ VPA | ☐ KAPX | Only as needed |
| ☐ CHOL | Esoterics | ☐ LAMX | ☐ AMM/ALC |
| ☐ CK | ☐ AMM | ☐ MA | ☐ HBA1C3 |
| ☐ CR-E (ENZ) | ☐ CHEX - (UDR) | ☐ PAB | ☐ SYNCHRON CNTL (L1-3) |
| ☐ COZE | ☐ CMBX - (UDR) | ☐ TRFN | ☐ VIGIL PROTEIN |
| ☐ DBIL | ☐ CSA - (UDR) | Drugs of Abuse | ☐ VIGIL SEROLOGY L1 & L2 |
| ☐ GGT | ☐ CYSX - (UDR) | ☐ AMPH | ☐ VIGIL SEROLOGY C Level C |
| ☐ HDL | ☐ ETOH | ☐ BARB | ☐ VIGIL TDM (L1-3) |
| ☐ IBCT | ☐ HbA1C3 (online) | ☐ BENZ | ☐ ULTIMATE BILI (L1-3) |
| ☐ IRON/FE | ☐ HbA1C (offline) | ☐ BUPX - QUAL | ☐ URINE PROTEIN |
| ☐ LD | ☐ HCTX (UDR) | ☐ BUPX - S-QUANT | ☐ DAT's - listed with Reagents |
| ☐ LDL-D | ☐ LAC | ☐ COCM | Additional QC request as needed: |
| ☐ MG | ☐ LIPASE | ☐ METH | ☐ Cyclosporine C4 |
| ☐ TBIL | ☐ LITHIUM | ☐ METQ | ☐ Cyclosporine c% (High) |
| ☐ TBIL - ENZ (UDR) | ☐ MTP | ☐ OP2 | ☐ VIGIL LIPID (L1-3) |
| ☐ TG | ☐ P-AMY | ☐ OP (300) | |
| ☐ UIBC | ☐ SALY | ☐ OXYX - QUAL | 3 Critical Care Testing |
| ☐ URIC | Protein/Serology | ☐ OXYX - S-QUANT | ☐ NA, K, CL, CO2, CALC |
| ☐ UREA (BUN) | ☐ AAGX | ☐ PCP | ☐ ALB |
| TDM | ☐ APOA | ☐ PROX | ☐ BUN |
| ☐ ACET | ☐ APOB | ☐ THC 20 | ☐ CREA (CR-S) |
| ☐ AMKX - (UDR) | ☐ ASO | ☐ THC 50 | ☐ GLU (Default - Modular) |
| ☐ CARB | ☐ C3 | ☐ THC 100 | ☐ GLUH (Cartridge) |
| ☐ DIG | ☐ C4 | ☐ XTCX - QUAL | |
| ☐ GEN | ☐ CERX (UDR) | ☐ XTCX - S-QUANT | |
| ☐ PHE | ☐ CRP | ☐ S BARB | ☐ PHOS |
| ☐ PHY | ☐ CRPH | ☐ S BENZ | ☐ TP |
| ☐ QINX - (UDR) | ☐ HPT | ☐ S TCA | |

| Remote Test | AMC/QMC | Referencing 11111 | Testing 22222 | Referencing 33333 | Testing 4444 | Sequel Generated Y/N | Data Reduction... | Data Reduction... | Data Reduction... | Customer Review | Corp Report Sent | Comments |
|---|---|---|---|---|---|---|---|---|---|---|---|---|
| ALP | | | | | | | | | | | | |
| Acetaminophen | | | | | | | | | | | | |
| Ferritin | | | | | | | | | | | | |
| AFP | | | | | | | | | | | | |

Account: XYZ  
BTI Coordinator: Susan Smith  
888-888-8686  
Service(s): Remote Installation 401, 1001, 1002, 1003, 1004, 1005, 1006

Testing Menu | PROG LOG 1 | SYN Volume Lookup | CAL Rack Assignments | QCNaming Convention | Naming ConvLIN | LINLotNums | PNs | HB Linearity Protocol | LotNumShip | QC Sync...

FIG. 11

| Calibrator Name | Barcode 1 | Barcode 2 | Barcode3 | Barcode 4 | Barcode 5 | Barcode 6 | Rack Assignment | Avery Rack Label | Alternate Rack Assignment Label |
|---|---|---|---|---|---|---|---|---|---|
| MULTICAL | MULTICAL | | | | | | 501 | Multi Cal | 501 |
| AQUACAL | AQUACAL1 | AQUACAL2 | AQUACAL3 | | | | 502 | AQUA Cal | AQUA/Multi Cal |
| DRUGCAL 2 | DRUGCAL2L1 | DRUGCAL2L2 | DRUGCAL2L3 | DRUGCAL2L4 | | | 521 (pos. 2-4) | Drug Col 2 (level 1-4) | |
| DRUGCAL 2 | DRUGCAL2L5 | | | | | | 522 (pos. 2-2) | Drug Col 2 (level 5-5) | |
| DRUGCAL 3 | DRUGCAL3+L1 | DRUGCAL3+L2 | DRUGCAL3+L3 | DRUGCAL3+L4 | | | 523 (pos. 2-4) | Drug Col 3+ (level 1-4) | |
| DRUGCAL 3 | DRUGCAL3+L5 | DRUGCAL3+L6 | | | | | 524 | Drug Col 3+ | |

Testing Menu | PROG LOG 1 | PROG LOG 2 | SYN Volume Lookup | CAL Rack Assignments | QCNaming Convention | Naming ConvLIN | LINLotNums | PNs | HB Linearity Protocol | LotNL ...

Linearity Naming Conventions

Click to go to programming [1] [2]

| Linearity Std | Level 1 | Level 2 | Level 3 | Level 4 | Level 5 | Dilution Level | Dilution Level 2 | Included Chems |
|---|---|---|---|---|---|---|---|---|
| LP | LP1 | LP2 | LP3 | LP4 | LP5 | LPD 10 (HDLD) | | HDLD, LDLD |
| ESOTERICS | E1 | E2 | E3 | E4 | E5 | | | |
| PRE ASSIGNED | PA1 | PA2 | PA3 | PA4 | PA5 | | | |

| Testing Menu | PROG LOG 1 | PROG LOG 2 | SYN Volume Lookup | CAL Rack Assignments | QCNaming Convention | Naming ConvLIN | LINLotNums | PNs | HB Linearity Protocol | LotNL ... |

| Test or Consumable | Reagent /Consumable PN | Calibrator PN | Control PN | Linearity PN |
|---|---|---|---|---|
| Consumables | | | | |
| No Foam | XXXXX | | | |
| Anti Foam | XXXXX | | | |
| Wash Concentrate-II | XXXXX | | | |
| Bar Code Labels | XXXXX | | | |
| Diluent 1 | XXXXX | | | |
| PVT 5 | XXXXX | | | |
| Environmental Caps | XXXXX | | | |
| PRO Autoplas | XXXXX | | | |
| CCMA | XXXXX | | | |
| UDR Cartridges | XXXXX | | | |
| Instrument Wash Buffer | XXXXX | | | |
| Maintenance | | | | |
| Saline (Use for maintenance) | XXXXX | NA | NA | NA |
| Cleaning Agent | XXXXX | NA | NA | NA |
| Sodium Hypochlorite | XXXXX | NA | NA | NA |

SERUM / PLASMA / URINE

| TEST Select test from drop down | Sample Pickup | Enter No Replicates | Sample * Reps | Total Sample Pickup (uL) | Select Container Type 0.5 mL = 500 uL 2.0 mL = 2000 uL | Container Dead Volume | Total Sample Required |
|---|---|---|---|---|---|---|---|
| ALP | 5 | 5 | 25 | 180 | 0.5 mL cup | 40 | 220 |
| ALT | 23 | 23 | 115 | | | | |
| BUN | 3 | 3 | 15 | | | | |
| ALBm | 5 | 5 | 25 | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |
| | #N/A | | #N/A | | | | |

Analyte
Select Analyte from the drop down
Case Sensitive
Select " " for blank entry.

FIG. 17

REMOTE TESTING OF LABORATORY INSTRUMENTS

This application is a continuation of PCT Application No. PCT/US17/058467, entitled "Remote Monitoring of Laboratory Instruments," filed Oct. 26, 2017, which claims priority to U.S. Provisional Application No. 62/413,115, entitled "Remote Testing of Laboratory Instruments," filed Oct. 26, 2016, each of which are incorporated by reference herein in their entirety.

TECHNICAL FIELD

The technology disclosed herein may be applicable to laboratory instruments.

BACKGROUND

Laboratory instruments, such as instruments used to analyze blood samples from patients, must be able to provide results that are both precise and accurate, and their proper performance must be verifiable, both by those who use the instruments as well as by regulators or individuals who are responsible for accrediting the laboratories where these instruments are located. However, setting up laboratory instruments that function properly, and testing these instruments to verify continued proper performance after they have been set up, may be difficult and time consuming. As a result, many laboratories may be completely dependent on third parties (e.g., equipment vendors) for performing critical tasks, which can lead to the laboratories being less self-sufficient, and may increase demands placed on a relatively few workers who do have the requisite expertise, and may also make it more difficult for new instrumentation to be brought on line and incorporated into a laboratory's operations. Accordingly, there is a need in the art for an improved technology for setting up and/or performing experimental studies on laboratory instruments.

SUMMARY

Embodiments disclosed herein may be used to implement methods and machines for remotely facilitating the setup and monitoring the performance of experimental studies on laboratory instruments. For example, embodiments disclosed herein may be used to perform a method which comprises performing a set of study facilitation acts on a subject laboratory instrument. In some embodiments, such a set of study facilitation acts may include, after calibration of the subject laboratory instrument, sending setup data to an instrument's location. In some other embodiments, such setup data may include, for each test from a set of one or more studies, an identification of that test and an identification of a number of replicates for that test. In some other embodiments, a set of study facilitation acts that may be part of a method performed based on this disclosure may also include updating study progress data for the subject laboratory instrument by performing various acts for each study from a requested study set. In some other embodiments, these acts may include (i) updating study progress data to indicate that programming a subject laboratory instrument may be complete after receiving information indicating that the subject laboratory instrument may be programmed to perform the one or more tests comprised by a study; (ii) after receiving information indicating a test from the study has been initiated, updating the study progress data to indicate that the study is in process; and (iii) after receiving information indicating that each of the tests comprised by the study is complete, updating the study progress data to indicate that the study is complete. In some other embodiments, a set of study facilitation acts which could be part of a method performed based on this disclosure may also include updating data collection progress data for the subject laboratory instrument by performing additional acts. In some other embodiments, such additional acts may include: (i) after the one or more tests comprised by a study have completed and data generated by those tests may be available for analysis, updating the data collection progress data to indicate that raw data for the study has been captured; (ii) after data generated by the tests comprised by the study has been analyzed, updating the data collection progress data to indicate that the data for the study has been reviewed; (iii) after each of the one or more tests comprised by the study has been successfully completed and a hard copy of the data generated by the successful tests has been created and stored at the location of the subject laboratory instrument, updating the data collection progress data to indicate that the data for the study has been captured; and (iv) after each of the one or more tests comprised by the study has been successfully completed and a hard copy of a summary report generated based on the data for the tests has been created and stored at the location of the subject laboratory instrument, updating the data collection progress data to indicate that the summary for the study has been printed.

In a certain embodiment, a potential way in which aspects of the technology disclosed herein may be implemented is in the form of a machine including a server that is configured with instructions operable to, when executed, perform acts including allowing an overseer to perform a set of study facilitation acts as described in the preceding paragraph. In a further embodiment, other machine and/or method implementations are also possible. In an example embodiment, aspects of the technology disclosed herein could be used to implement a machine that comprises a network and, connected to the network, one or more laboratory instruments and means for allowing an overseer to oversee the performance of experimental studies on one or more remotely located laboratory instruments. In a further embodiment, aspects of the disclosed technology may be implemented in the form of a computer program product comprising a computer readable medium (which may be non-transitory) storing instructions for allowing an overseer to perform study facilitation acts such as described in the preceding paragraph. Similarly, just as further embodiments may include other types of machines, further embodiments may also be implemented in the form of other types of computer program product.

Further information on how the disclosed technology could potentially be implemented is set forth herein, and variations on the sample will be immediately apparent to and could be practiced without undue experimentation by those of ordinary skill in the art based on the material which is set forth in this document. Accordingly, exemplary methods and machines described in this summary should be understood as being illustrative only, and should not be treated as limiting on the scope of protection provided by this or any related document.

BRIEF DESCRIPTION OF DRAWINGS

FIG. 4 provides an example embodiment of an interface that could be provided by a tool used by an overseer during experimental studies.

FIGS. 5a-5c provide example embodiments of interfaces that could be used in configuring a laboratory instrument.

FIG. 6 provides an example embodiment of an interface that could be used to program an instrument for testing.

FIG. 8 provides an example embodiment of an ordering form with multiple platforms.

FIG. 10 provides an example embodiment of an interface that could be provided by a tool used by an overseer during experimental studies.

FIG. 11 provides an example embodiment of an interface that could be provided by a tool used by an overseer during experimental studies.

FIG. 12 provides an example embodiment of an interface that could be provided by a tool used by an overseer during experimental studies.

FIG. 14 provides an example embodiment of an interface that could be provided by a tool used by an overseer during experimental studies.

FIG. 16 provides an example embodiment of an interface that could be provided by a tool used by an overseer during experimental studies.

FIG. 17 provides an example embodiment of an interface that could be provided by a tool for calculating an amount of sample for a study.

DETAILED DESCRIPTION

The technology disclosed herein can be used to address problems related to setting up and running experimental studies (e.g., precision, linearity, various method comparisons, reference intervals, and limit of blank studies) on Hematology analyzers, Flow Cytometry, Chemistry, Urinalysis and/or Microbiology testing platforms, and other laboratory instruments. Accordingly, for the purpose of illustration, this document focuses on the application of the inventors' technology in that context. However, while the present description is provided by way of illustrative example, numerous modifications and alternate embodiments of the disclosed technology will occur to those skilled in the art. As a result, the features from the examples set forth in this description should not be treated as implying limitations on the protection provided by this document or by any other document which claims the benefit of this disclosure.

Figure 1:
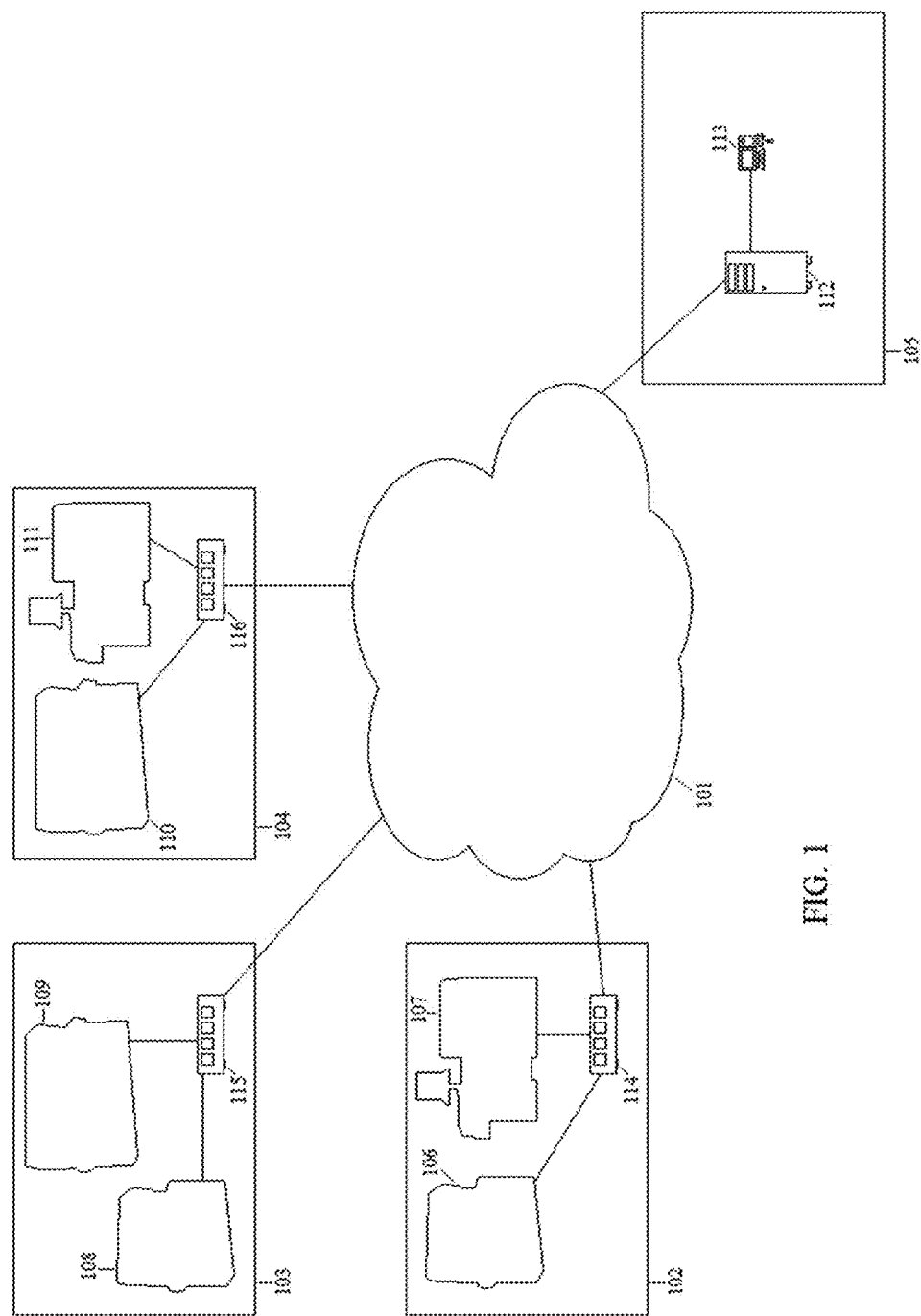
FIG. 1 is an exemplary embodiment of a block diagram of an environment in which aspects of the technology described herein could be deployed.

Turning now to the figures, FIG. 1 is a block diagram of an environment in which aspects of the technology described herein could be deployed in some embodiments. In that environment, a network 101 may be used in some embodiments to establish connections between remotely located laboratories 102-104 and a network instrument monitoring center 105. In this environment, the network instrument monitoring center 105 may, in some embodiments, provide supervisory services for the instruments 106-111 at the laboratories 102-104. For example, in some embodiments a server 112 located at the network instrument monitoring center 105 may analyze data gathered from the instruments 106-111 (e.g., by comparing performance data sent from the instruments 106-111 against rules for expected performance, by determining whether any deviations between the performance data from the instruments and historical performance data stored in a database are within an acceptable range, etc.) and, based on that analysis, may generate alerts for workstations 113 of personnel who may potentially perform troubleshooting or other activities to help remedy any actual or incipient faults in the instruments 106-111.

In some embodiments, in an environment such as shown in FIG. 1, to facilitate and enhance the security of communication over the network 101, each of the laboratories 102-104 may be equipped with a remote application process (RAP) box 114-116 which may serve as an interface for information being sent to or received from the network instrument monitoring center 105. In some embodiments, such RAP boxes 114-116 may do this by, for example, buffering information gathered by sensors and software agents on the laboratory instruments 106-111, encrypting that information for transport, then sending that encrypted information to the server(s) 112 at the network instrument monitoring center 105 over a secure virtual private network (VPN). In implementations where this type of VPN is present, it may also be used for communications from the network instrument monitoring center 105, or communication of other information from the laboratories 102-104 to the network instrument monitoring center 105. For example, in an implementation where software running at the laboratories 102-104 would allow personnel using workstations 113 at the network instrument monitoring center 105 to engage in a screen sharing session with laboratory workstations (not shown), the information about what was displayed at the laboratory workstations and what commands those workstations should execute may be sent, respectively, to and from the network instrument monitoring center 105 over the VPN.

The specific manners in which devices such as shown in FIG. 1 and their respective functionalities could be implemented may vary significantly from one case to another. For example, one preferred embodiment for the RAP boxes 114-116 is to implement them as special purpose computers which use a solid state drive (SSD) to provide fanless cooling and avoid the need for moving parts, connect to transmission control protocol/internet protocol (TCP/IP) ports of the laboratory instruments using built in Ethernet ports, and use 128 bit advanced encryption standard (AES) software to encrypt data before sending it to the network instrument monitoring center 105 using OpenVPN (from OpenVPN Technologies, Inc., available at https://openvpn.net) or similar transport layer security software. However, it is possible that an environment such as shown in FIG. 1 may be set up using RAP boxes 114-116 which are implemented in some other manner. For example, in some embodiments it is possible that a RAP box could be implemented using a conventional hard disk drive (HDD) rather than (or in addition to) a SSD, which would result in the RAP box having a lower cost, but also being less durable, due to the need for additional moving parts in and in to support the HDD. Numerous other modifications and alternate embodiments are also possible, and will occur to those of skill in the art in light of this disclosure.

Just as variations are possible in how devices in the environment of FIG. 1 could be implemented, variations are also possible on the numbers and configurations of devices which could be included in such an environment in various embodiments. For example, while FIG. 1 illustrates the network instrument monitoring center 105 as including a server 112, it is likely (and, indeed, preferred) for software at the network instrument monitoring center 105 to be run using one or more server clusters, thereby achieving benefits such as load balancing, redundancy, and higher availability. Similarly, while FIG. 1 illustrates the RAP boxes 114-116 communicating directly with the server 112 at the network instrument monitoring center 105, in some implementations, other components, such as firewalls in the communication path between the RAP boxes 114-116 and the server 112 on the laboratory side and/or the monitoring center side could be deployed to provide added security for the respective internal networks of the laboratories 102-104 and network instrument monitoring center 105. Other components, such as routers for directing communications appropriately within the internal networks of the monitoring center and/or laboratories and/or separate database clusters for storing instrument data outside of the memory of the server(s) at the monitoring center could also be deployed in an environment such as shown in FIG. 1.

Just as some environments where the disclosed technology is implemented may include components not shown in FIG. 1, it is also possible that the disclosed technology could be implemented in an environment in which some of the components shown in FIG. 1 are omitted. For example, while FIG. 1 depicts each laboratory 102-104 having a RAP box 114-116 as an interface for information sent to or received from a network instrument monitoring center 105, in some embodiments RAP boxes 114-116 such as shown in FIG. 1 might be omitted, and instead of communicating through a per-laboratory interface, the instruments 106-111 may communicate with the network instrument monitoring center 105 directly. In this type of embodiment, rather than relying on an external device, the laboratory instruments 106-111 may be configured with software which, when executed, would generate a virtual machine to perform the types of functions (e.g., encryption and buffering of information for transport) described above as being provided by the RAP boxes 114-116 in the environment of FIG. 1.

Just as variations are possible in the implementation of an environment such as shown in FIG. 1, it is also possible that aspects of the disclosed technology could be implemented in environments other than that shown in FIG. 1. As an example of this, consider a cloud based environment in which, rather than relying on local equipment such as the server 112 depicted in FIG. 1, a network instrument monitoring center 105 may use virtual resources provided by a cloud computing platform. In this type of environment, it is possible that multiple network instrument monitoring centers may be supported by the same infrastructure provided by the cloud platform, and that that infrastructure may be grouped into separate regions (e.g., China, North America, etc.) to provide features such as localization of rules and policies. Similar approaches may also be applied to other items shown in FIG. 1. For example, instead of relying on personnel using physical workstations 113 at a physical network instrument monitoring center 105, it is possible that, in some implementations, the functions which may otherwise be performed using those workstations (e.g., engaging in screen sharing sessions) may be performed by individuals using their own equipment at locations of their choosing to connect to the relevant supporting infrastructure (which could be a physical server such as the server 112 shown in FIG. 1, or cloud based infrastructure such as described above). Accordingly, the discussion of the environment of FIG. 1 should be understood as being illustrative only, and should not be treated as implying limitations on the scope of protection provided by this document or any related document.

Figure 2:
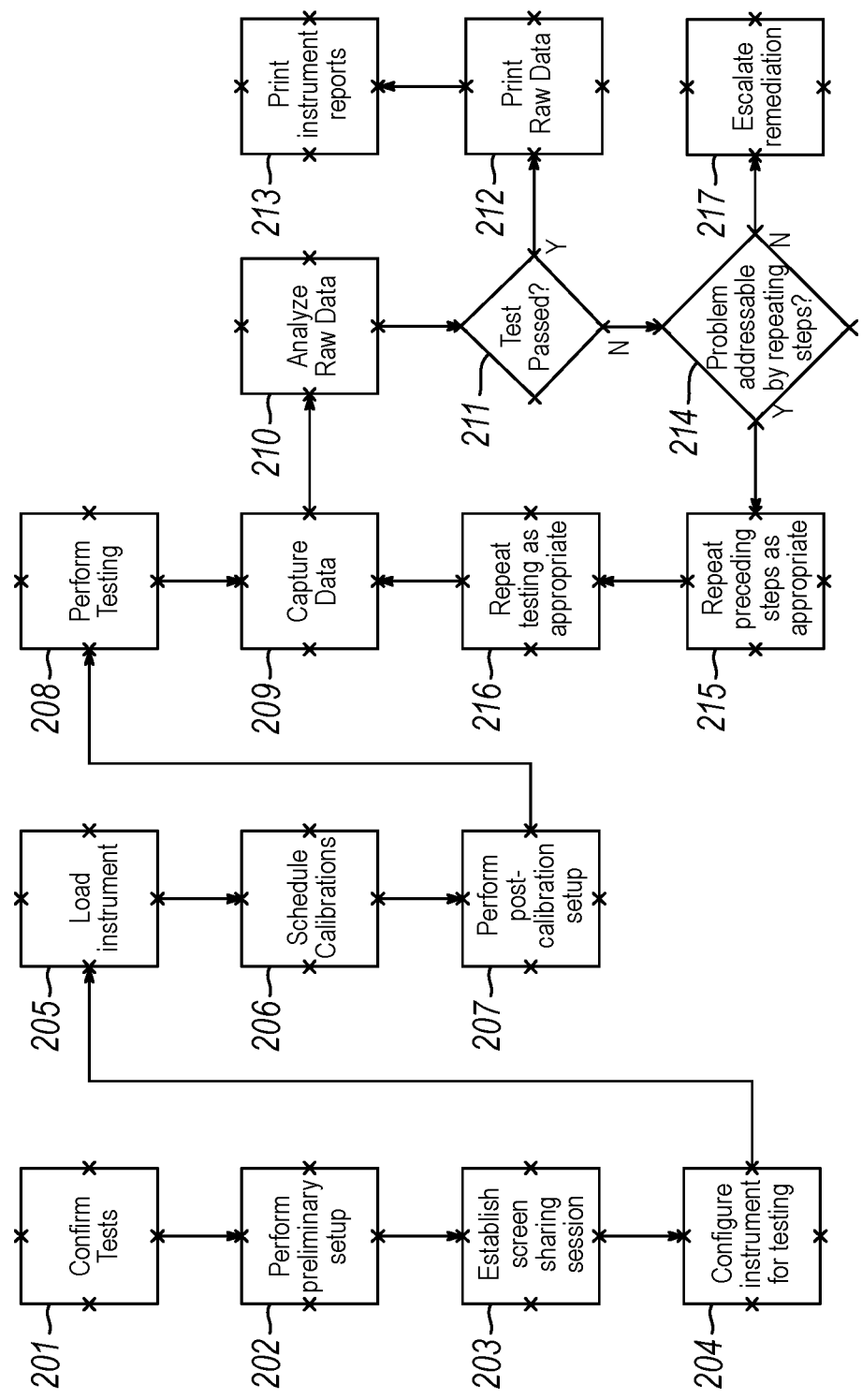
FIG. 2 depicts an exemplary flowchart of steps which could be used to allow for, and to oversee the performance of, experimental studies on laboratory instruments at one or more laboratories in an environment such as shown in FIG. 1.

Turning now to FIG. 2, that figure depicts a flowchart of steps which may be used in some embodiments to allow for, and to oversee the performance of, experimental studies on laboratory instruments at one or more laboratories in an environment such as shown in FIG. 1. In the first step of the method of FIG. 2, which preferably would take place prior to an instrument being installed at a laboratory, the tests which would be performed as part of the experimental studies may be confirmed 201. This may be done, for example, by an individual at a network instrument monitoring center 105 using a workstation 113 to access a dashboard interface, comparing the information presented in that dashboard interface (which could be populated with data stored on the server (or corresponding infrastructure in the relevant environment) by a salesperson at the time an order for the instrument in question was placed) with information in an implementation order summary guide (i.e., a standard guide for what types of testing normally take place when the type of instrument in question is normally installed), and contacting the laboratory (or other entity which requested that the instrument be installed) to confirm any discrepancies between the two.

After confirming 201 tests to be performed for an instrument, in some embodiments preliminary setup may be performed 202 for the laboratory where the instrument would be used and/or the network instrument monitoring center. On the laboratory side, this may include updating (or placing) an order to ensure that all needed reagents and/or other necessary items, such as calibrators and controls, were present at the laboratory at the time that the testing was to take place. For example, for testing to verify a lab's ability to obtain proper quantitative determinations of HDL Cholesterol in the high density lipoprotein fraction of human serum or plasma using a chemistry analyzer, the preliminary setup may include ensuring that the HDL reagent, HDL and Quality Control materials were all available at the lab. For other types of tests, or tests of other types of equipment, different materials may be obtained as appropriate. As an example of this, FIG. 8 provides a sample order form which may be used to order materials for tests of other immunoassay and chemistry systems, though it should be understood that this figure is intended only to provide further illustration, and that it should not be treated as implying limitations on the types of items that could be obtained during preliminary setup, or the manner in which those items could be obtained or referred to. On the network instrument monitoring center side, the preliminary setup may include updating a data menu template to receive and organize data for the test(s) that would be performed. An example of an interface which may be provided in such a data menu template is provided in FIG. 4, which is discussed below.

Figure 4:
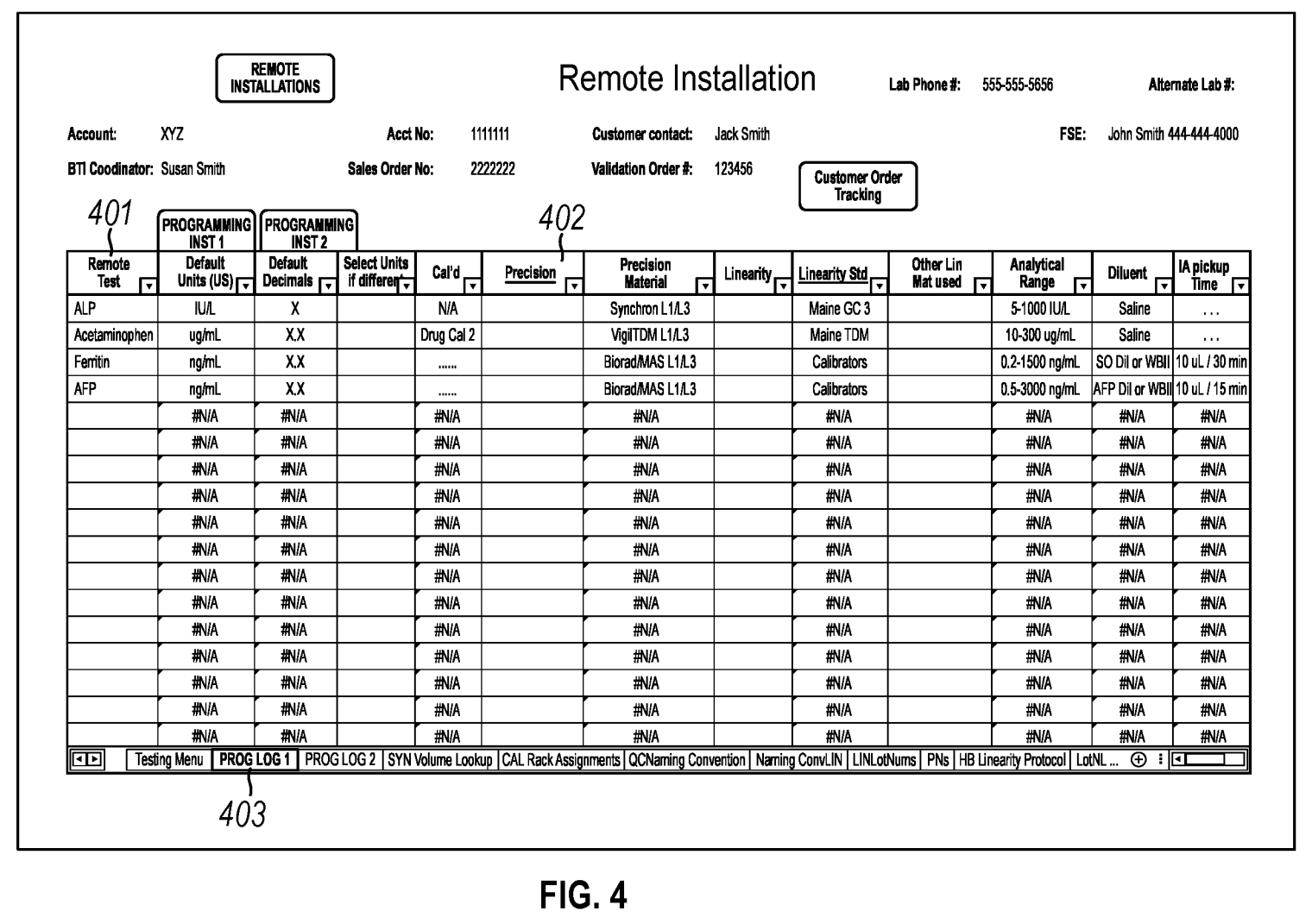

Preferably in a data menu template, to define a test, a user may select a blank cell in a test type column 401, which may result in the template presenting the user with a drop down menu of possible tests which could be performed. Once the user had selected a test from the drop down menu, cells in the row for that test could be automatically populated with various information about the test. This information, examples of which are provided in FIG. 4, may include, for example, recommended units of measurement, decimal places, analytical measuring range, quality control(s), linearity material(s) and diluent(s). In some embodiments, other information such as a test's pickup volume and time to completion may also be auto-populated, though this might be limited to only certain types of tests or certain types of platforms. For example, as shown in FIG. 4, tests on an immunoassay platform (e.g., in FIG. 4, those for Ferritin and AFP) may have pickup volume and time to completion auto-populated, while tests on other platforms (e.g., the ALP and Acetaminophen tests listed in FIG. 4, which would be tests of a chemistry platform) may have that information left undefined as being irrelevant.

The auto-populated information may then preferably be modified by the user as necessary. For example, if it was necessary to establish that an instrument could function with a higher level of precision than would be reflected by the default values, then the user may increase the number of decimal places to be used for the test from the default value to some greater value appropriate for the necessary precision. Finally, in some embodiments, once all tests to be performed had been entered, and the data in the rows for those tests accurately reflected their respective requirements, the preliminary setup for the network instrument monitoring center may be deemed complete and the process of FIG. 2 may proceed.

In the flowchart of FIG. 2, after preliminary setup had been performed 202 (and, if the instrument to be tested had not yet been physically installed at the laboratory, after the instrument had been installed), a screen sharing session may be established 203. In this screen sharing session, an individual located at the remote network instrument monitoring center 105 may view and interact with interfaces presented on a device located at the laboratory which might be used to control the instrument being tested once it entered normal operation. In some embodiments, once the screen sharing session had been established 203, an individual (referred to herein as the overseer) at the network instrument monitoring center 105 who was responsible for overseeing the experimental study or studies on the instrument (which, in this context, should be understood broadly to include preparatory steps such as calibrating the instrument, as well as actually performing the tests which the study/studies would comprise) may configure the instrument to be tested 204. Examples of interfaces which may be used in some embodiments to perform this configuration (which may be presented on a workstation at the laboratory and controlled from the network instrument monitoring center 105 during the screen sharing session) are presented in FIGS. 5a-5c.

Figure 5B:
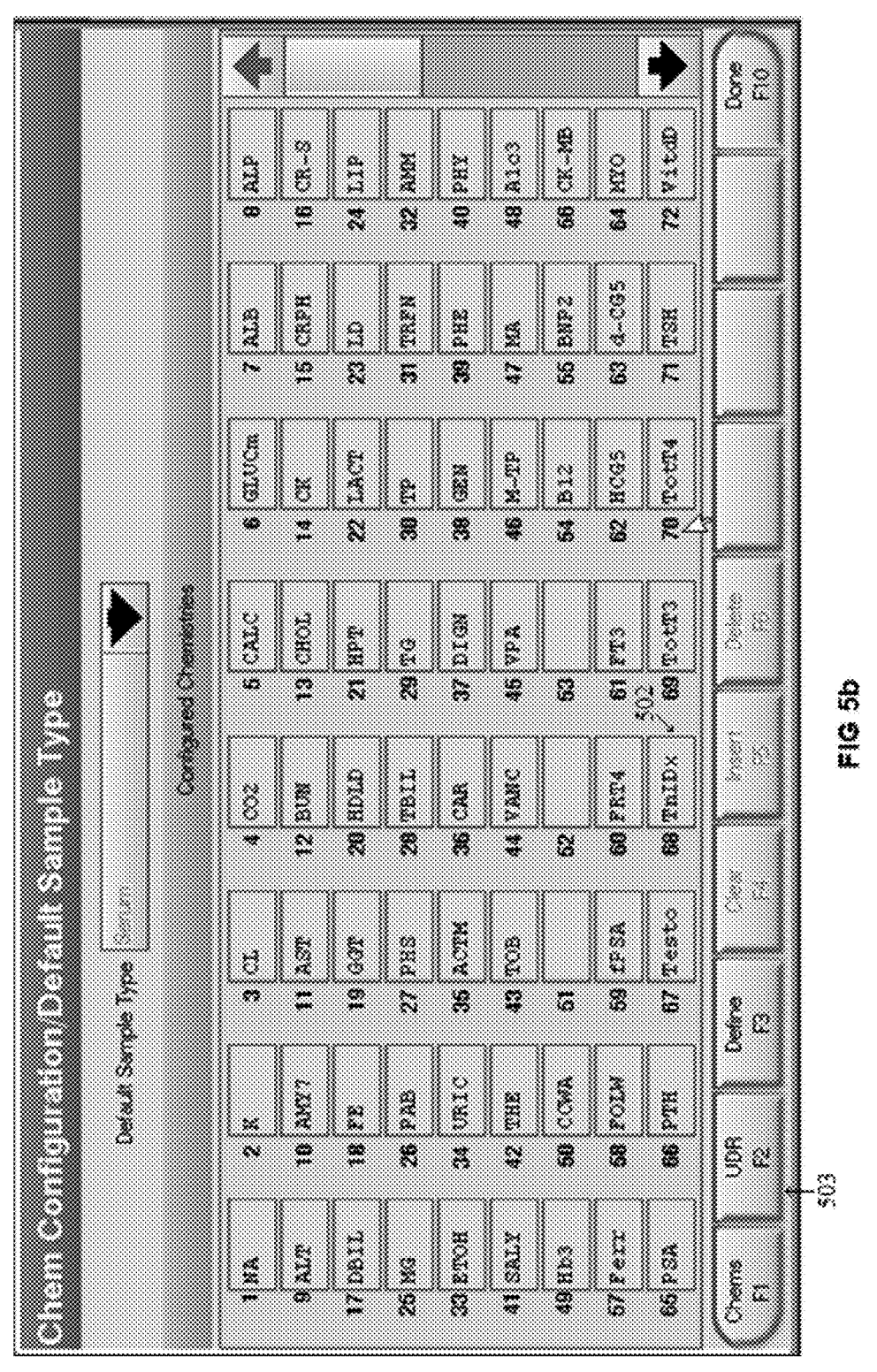

In FIGS. 5a-5c, the interface of FIG. 5a may be used in some embodiments to specify the built in tests that were available on the subject instrument by checking the "Enabled" boxes for the available tests, the interface of FIG. 5b may be used in some embodiments to view the tests that were available or specify that a new user defined test may be created, and the interface of FIG. 5c may be used in some embodiments to define or edit the operating parameters of a user defined test. To illustrate, consider the case where the subject instrument is an integrated chemistry and immunoassay testing platform provided by a company which also provides various reagents which may be used in that instrument's operation. In such a case, if one of those reagents was abbreviated TnIDx (as is the case with the Access AccuTnI+3 reagent), the instrument may be pre-programmed in some embodiments with the parameters that would be used to test it, as shown in the TnIDx row 501 of FIG. 5a. Then, if the lab expected to use that reagent for tests when the instrument was in operation (e.g., if it expected to use the instrument to determine levels of cardiac troponin I in samples of human serum and plasma), the enabled box in the TnIDx row 501 of the interface of FIG. 5a may be checked to show that the test was available. That test could also be displayed in the interface of FIG. 5b in the form of the TnIDx abbreviation 502. In some embodiments the interface of FIG. 5b may also be used if the user wanted to add a user defined test. For example, in some embodiments, to perform a test for a third party test reagent, the user may activate the UDR control 503 in FIG. 5b and use an interface such as that shown in FIG. 5c to specify the parameters (e.g., reaction type, units, precision, etc.), processing factors, and detection limits for that test.

Of course, it should be understood that the interfaces of FIGS. 5a-5c, and the discussion set forth above for how those interfaces could be used, is intended to be illustrative only, and should not be treated as implying limits on how an instrument may be configured 204 in a method such as shown in FIG. 2. In various embodiments, configuring 204 an instrument may be performed using interfaces other than those illustrated in FIGS. 5a and 5c and/or may involving defining other parameters for the tests. For example, preferably, instrument configuration 204 may include defining the following parameters according to the needs of the laboratory where the instrument would be used: chemistry configuration (test menu and default sample type (serum/plasma) or equivalent information for non-chemistry platforms), date and time, demographic setup (what prints on each patient report), report type and setup (facilities information typically name, address and serial number of system), panels specific for each laboratory (example a lipid panel could include the tests Cholesterol, HDL and Triglyceride), units and precision for each test, rack setup (identifying which racks will be used for various container types (tubes, cups, inserts), barcode and/or rack assignments for calibrators, host communication parameters specific for each laboratory (enables the instrument to communicate with the Laboratory information system), and any Special Calculations (e.g., if the laboratory reports out a calculated Low Density Lipoprotein (LDL); a special calculation (formula) would be required using Cholesterol, HDL and Triglycerides results).

In some embodiments, once the instrument has been configured 204, it would be loaded 205 with the necessary reagents. In this step, an individual at the laboratory where the instrument is located may place the reagents for the test into the instrument, preferably based on instructions provided by the individual overseeing the testing process. After the reagents had been loaded 205, the instrument may be calibrated 206 for the tests to be performed. This may include personnel at the laboratory preparing and loading the appropriate calibrator(s), generation of a calibration testing report with details of the instrument's measurements, and reviewing the report to determine whether the calibration was successful (i.e., whether the instrument passed or failed).

Figure 7:
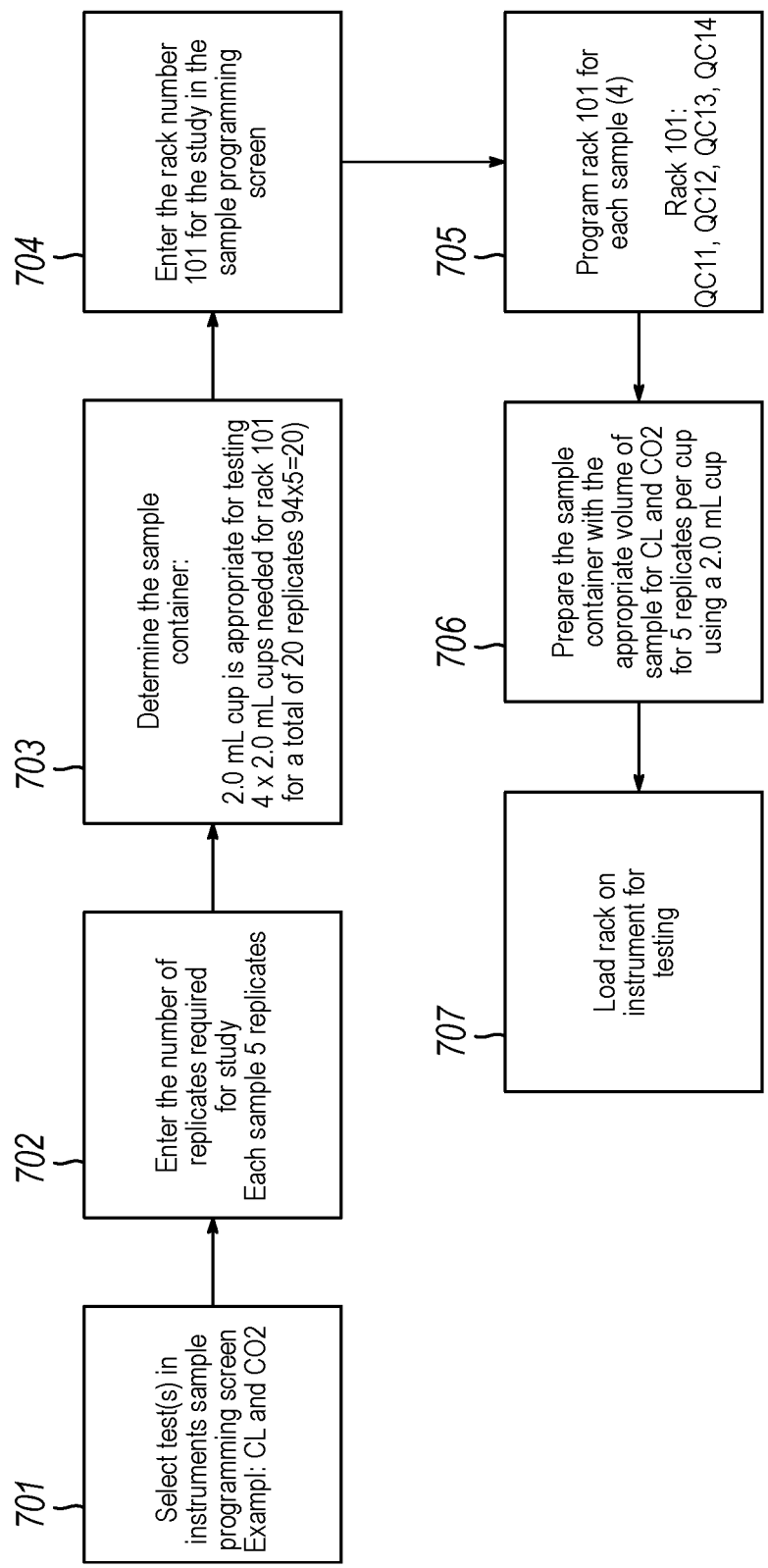
FIG. 7 provides an exemplary embodiment of a flow chart of steps that could be performed during post-calibration setup of an instrument.

The flowchart of FIG. 2 also includes a step of performing post-calibration setup 207. This post-calibration setup may include both preparation of the sample(s) that would be used for the test(s), as well as programming the subject instrument to perform the test(s) with the sample(s). To illustrate, consider FIGS. 6 and 7, which provide a flowchart of steps which could be performed in some embodiments as part of post-calibration setup of a precision study comprising tests of Chloride and $CO_2$ and an exemplary interface which may be used in such steps. As shown in FIG. 7, initially, the tests to be performed as part of the study may be selected 701. Using the interface of FIG. 6, this could be done by actuating controls for CL and CO2 from a set of controls showing tests whose parameters had been set previously (e.g., during configuration 204, or, in the case of built in tests, prior to delivery). Once the tests had been selected 701, the same interface may be used to specify the number of replicates by entering 702 how many replicates would be performed for the study which, in this example, is five replicates each for $CO_2$ and Chloride. With this information, a determination 703 may be made of what container(s) would be needed for the samples on which the tests would be run. An example of the type of calculations which could be performed as part of such a determination is provided in FIG. 7.

Figure 9:
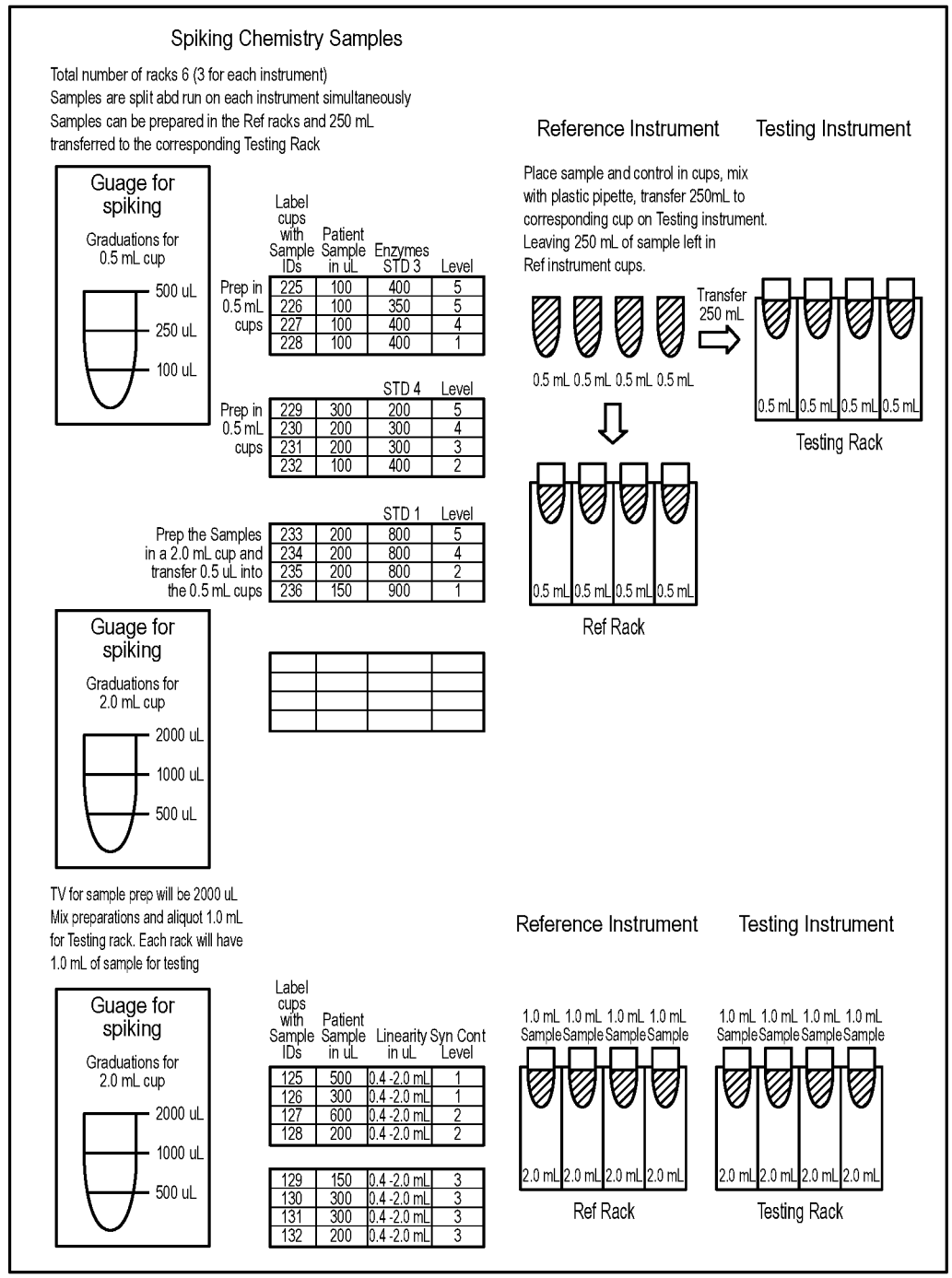
FIG. 9 provides an example embodiment of a spiking chart that could be used in sample preparation.

In some embodiments, once the sample container(s) had been determined 703, the process of FIG. 7 continues with entering 704 the number of the rack(s) in which the samples would be located, and programming 705 the rack(s) for the study. Using the interface of FIG. 6, these steps may be done by entering the rack number (which, in the case of this example, is 101) into a rack text field 601, then entering the sample IDs (which, in the case of this example, are QC11, QC12, QC13, and QC14) into fields in the interface corresponding to their locations in the rack. Finally, before the samples would be loaded 707 into the appropriate rack for testing, the process of FIG. 7 includes a step of preparing 706 the sample container(s) with the appropriate materials for the study. In some embodiments, to support this, an individual at the laboratory where the subject instrument is located may be provided with a sample programming list which includes the sample ID, rack number and position and tests being performed (either on a computer screen, a printout, or both, depending on the individual's preferences), with the individual overseeing the experimental studies providing assistance as needed. For example, to assist with the preparation of a spiked sample for a method comparison study, a spiking chart such as shown in FIG. 9 may be sent to the laboratory, and the individual at the laboratory who would prepare the sample may use that chart (along with any additional explanation provided from the network instrument monitoring center) to prepare the sample and load it into the instrument.

Of course, it should be understood that the discussion of post-calibration setup 207 set forth above is intended to be illustrative only, and should not be treated as limiting. For example, while the above discussion focused on an example of a study comprising tests of Chloride and $CO_2$, in some embodiments the disclosed technology could be used for studies which included other types of tests either in addition to, or as alternatives to, the Chloride and $CO_2$ tests described above. For instance, in some embodiments the same types of interfaces and steps described above in the context of the Chloride and $CO_2$ tests may be used to program a linearity test for sodium by specifying that it would include 5 samples placed in racks 10 (positions 1-4) and rack 11 (position 1), selecting 3 replicates for each sample, and adding identifiers such as G11, G12, G13, G14, G15 for the positions of the corresponding samples in the rack(s). Accordingly, the discussion of post-calibration setup 207 set forth above in the context of FIGS. 6 and 7 should not be treated as implying limits on the protection provided by this or any related document.

In some embodiments, after performance of the post-calibration setup 207 is complete, the test(s) would be performed 208 and the data from the test(s) may be captured 209 and analyzed 210. Preferably, the performance 208 of the test may be controlled from, and the analysis 210 of the test data may take place at, the network instrument monitoring center 105. With respect to the performance 208 of the test, this may be controlled using a screen sharing session such as may have been established 203 earlier in the method of FIG. 2, in which an individual participating in that screen sharing session from the network instrument monitoring center 105 may use the interface on the shared screen to cause the subject instrument to start the test, though of course the test may also be started by an individual at the laboratory, such as at the instruction of the individual overseeing the test. With respect to the analysis 210 of the test data, this may be enabled by the raw data from the test being sent from the laboratory with the tested instrument to the network instrument monitoring center 105.

In embodiments where it takes place, transmission of raw data from a laboratory to a network instrument monitoring center 105 may be performed in a variety of manners. For example, after a test was finished, the test data may be saved as a comma separated value (CSV) file at the laboratory, then retrieved by activating a file retrieval control in a dashboard interface. This may result in the overseer being presented with an interface for selecting the type of file(s) to be retrieved and/or an interface for actually specifying the file(s) that should be transferred. Alternatively, in some embodiments test data may be transmitted to, and stored in a database at, the network instrument monitoring center 105 as it was gathered, and at the end of the test(s) that data may be retrieved from the database using an appropriate query (e.g., a query in the structured query language, or SQL, requesting all records sharing an identifier with the tested instrument which were created during the time period when the test took place). As yet another alternative, in some embodiments a screen sharing session which may have been established 203 previously may be used for data capture, such as by using the shared screen to send a command to the instrument being tested (e.g., a command invoking a result recall function) which would cause it to make its results available on the device whose screen was being shared. Of course, other ways of transferring data (e.g., sending it from the laboratory to the network instrument monitoring center 105 as an email attachment) will be immediately apparent to those of ordinary skill, and could be supported in various embodiments of the disclosed technology. Similarly, some embodiments could support more than one of (or, indeed, all of) the data transmission approaches described above, thereby providing the individuals performing the testing with flexibility to determine the approach which was most suited to their particular circumstances. Accordingly, the above discussion of how test data could be communicated should be understood as being illustrative only, and should not be treated as limiting.

Whatever data transmission techniques are used for making the testing data available at the location where the analysis 210 is to take place, in some embodiments once the raw data is available it may be provided to a statistical analysis program which may derive salient information about the test from the raw data. This information may then be reviewed to determine 211 if the test(s) had been successful. If so, the raw data and a summary report with a statistical summary of the test(s) performed as part of the study may be printed 212-213 at the laboratory where the testing took place or printed at the network instrument monitoring center 105 and sent to the laboratory) and stored for recordkeeping and compliance purposes. Alternatively, if the determination 211 of whether the test(s) had been successful indicated a problem, a further determination 214 may be made of whether that problem may be addressed by repeating one or more of the preceding steps. If it could, then in some embodiments the preceding steps might be repeated 215 and the test(s) might be rerun 216 as appropriate, and the data gathered by rerunning 216 the tests might be captured and analyzed as described previously. For example, if it was determined 214 that the test was unsuccessful due to a problem with the post calibration setup 207, then the instrument might be reprogrammed 705 and reloaded 707, which would preferably take place by the overseer informing an individual at the laboratory of the problem, requesting that the individual at the laboratory reprogram and reload the instrument, and providing additional guidance (potentially including reprogramming the instrument using the screen sharing session) to ensure that the problem is not repeated. Ideally, this would result in the instrument passing the necessary tests, though if it did not, the troubleshooting and analysis steps 209-216 might be repeated until a successful result was ultimately obtained or until it became necessary to escalate 217 the remediation beyond addressing problems with the performance of the steps shown in FIG. 2.

To provide a concrete illustration of how the troubleshooting, remediation and escalation steps 214-217 of FIG. 2 could take place, consider the case of a precision study for Chloride programmed for 20 replicates using a low control with passing criteria being a standard deviation less than or equal to 2.0 for a mean less than or equal to 100. In such a case, if the results provided a mean of 84.5 with a standard deviation of 2.4, then the data might be analyzed to determine what problem had prevented the passing criteria from being met. If this analysis indicates a problem with the steps leading to the failed result which could be addressed by repeating them, then those steps might be repeated as appropriate. For example, if the data analysis identified erratic performance correlated to a particular sample, and physical examination of that sample revealed that it included bubbles, then a reasonable conclusion might be that the bubbles were the cause of the failure. The run might then be repeated with attention to sample preparation, and the results of the new run compared with the passing criteria. Alternatively, if (either originally or after one or more remediation cycles) it does not appear that the result stemmed from a problem that might be addressed by repeating steps, then the problem might be escalated, such as to a technician who might determine if there was a hardware failure (e.g., a leak with a reagent probe) and replace or repair the hardware as needed to address the problem.

Of course, it should be understood that, while FIG. 2 illustrates a method which might be used allow for and oversee the performance of experimental studies on laboratory instruments when they are initially set up, the disclosed technology is not limited to being used in that context. For example, in some embodiments instead of being used in the context of initial setup, a method such as shown in FIG. 2 (and, in particular, the steps starting with establishing 203 a screen sharing session) might be used for the purpose of ensuring that an instrument continues to operate properly after the initial setup has taken place (e.g., to assist in generation of documentation to satisfy a laboratory's periodic regulatory and accrediting agency requirements). In some embodiments, a method such as shown in FIG. 2 might also be used for other purposes entirely. For example, it is possible that remote interactions such as shown in FIG. 2 might be used to train personnel who would later be responsible for operating or maintaining laboratory instruments—in which case the individual or individuals being trained would preferably learn about the relevant instrument(s) by performing the tasks described above as being performed by someone at the location of the instrument being tested. Accordingly, the above discussion of FIG. 2 should not be seen as implying that the disclosed technology is limited to being deployed in a particular context, or being used for a particular purpose.

Just as the above discussion should not be treated as implying limitations on the contexts in which the disclosed technology could be deployed, it also should not be treated as implying that the disclosed technology could only be used in methods which follow the flowchart of FIG. 2. For instance, in some cases, the disclosed technology could be used to perform a method which includes the same steps as shown in FIG. 2, but where those steps are performed in a different order. For example, while the above discussion and flowchart of FIG. 2 described and illustrated post-calibration setup 207, which included programming the rack(s) 705 as the last step which would take place before test was performed 208, in some embodiments the programming 705 might be performed in advance—potentially as soon as confirmation 201 of what tests are to take place. Similarly, in some cases, running experimental studies might involve steps which are not described and/or illustrated in FIG. 2 and its associated discussion. For example, in cases where a method comparison study is being performed to ensure that a result obtained using the subject instrument matches what is obtained by a second instrument at a different location, there may be additional steps of sending specimens to the second instrument for parallel testing and/or comparing the data from the instruments involved in the study.

Figure 11:
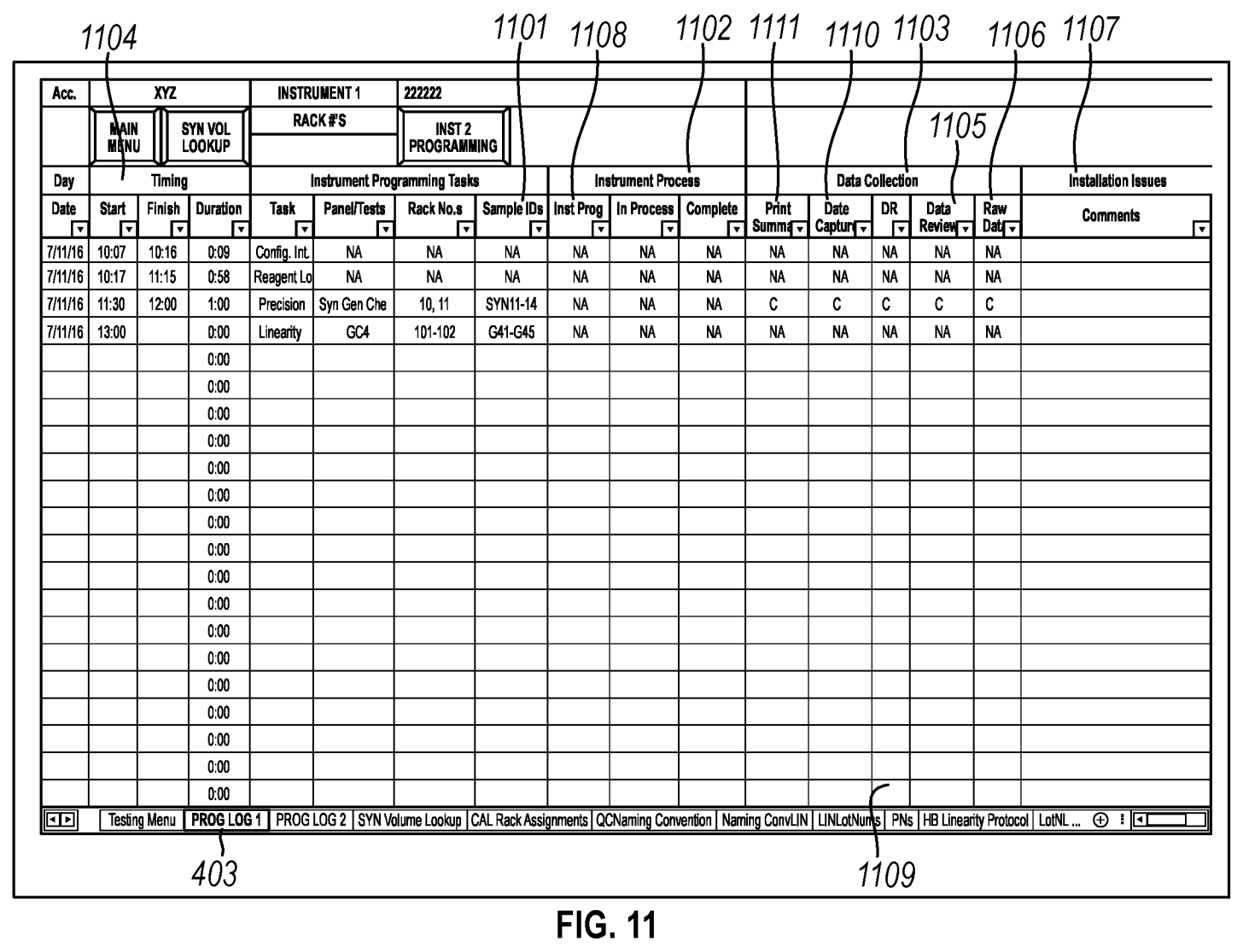

Variations are also possible in the entity or entities who would be involved in/impacted by the disclosed technology being used. For example, while the discussion of FIG. 2 focused on testing for a single instrument at a single laboratory, in some embodiments, a method such as shown in FIG. 2 may be performed simultaneously for multiple instruments which might potentially be located at multiple laboratories, such as if multiple instruments were scheduled to be set up at the same time in different locations. In this type of variation, when one study enters a phase where the focused attention of the overseer is not necessary, that individual could perform steps that do require his or her attention on other studies. For instance, in some embodiments, while a test of a first instrument 106 at a first laboratory 102 is being performed 208, an overseer at a network instrument monitoring center 105 may perform one or more step(s) (e.g., establishing 203 a screen sharing session, configuring 204 the instrument for testing) for a second instrument 108 which would be tested at a second laboratory 103. To help facilitate this type of activity, as part of the preliminary setup 202, the overseer might be allowed to add a programming log (e.g., by adding a new sheet such as shown in FIG. 11, discussed infra) for tracking activities for each of the instruments being tested. Alternatively, in some embodiments, an overseer might use different templates for tracking different instruments, or could use some combination of approaches. For example, in some embodiments an individual tasked with overseeing tests for multiple different entities might set up a different template for each entity and then, within templates, if an entity had multiple machines (preferably located at multiple laboratories), add a new programming log for each of that entity's machines. In this way, a single individual at a remote location might simultaneously oversee studies at two (or more) laboratories for two (or more) entities, instead of requiring a single dedicated overseer for each laboratory where a test is to take place.

Different embodiments of the disclosed technology could also vary in terms of the implementation of their underlying infrastructure, such as the hardware and software which might be used to perform a method such as shown in FIG. 2. One example of this type of variation which was already discussed is the potential for variations in how data is transmitted in embodiments where test data is analyzed at a location other than the location of the instrument being tested. However, this is not the only type of infrastructure implementation which could vary from embodiment to embodiment. For example, in an embodiment where a data menu template is auto-populated with information about a test, such as the test's recommended unit of measurement or analytical measurement range, this auto population could be supported in a variety of ways. For instance, in some embodiments, auto-population could be performed using data hard coded in to the data menu template itself (e.g., in an embodiment with a data menu template implemented as an EXCEL spreadsheet file, the auto-population could be performed by executing a script with conditional statements of the form If TestType=X Then Units=$X_{Units}$ etc.), while in other embodiments the data may be pulled from a remote source once the user specifies a test type (e.g., workstation 113 could send a call to server 112, which would retrieve the recommended values from a local database (e.g., tables on a Sharepoint site) and then return them to the workstation 113 to be auto-populated).

In embodiments where a data menu template is present, the manner in which it is implemented may vary in ways other than how (and if) it is auto-populated. For example, in some embodiments, to support a scenario where a single individual might be simultaneously overseeing multiple studies, a data menu template such as shown in FIG. 4 may include spaces where the overseer could enter information to track the progress of each test, such as the precision column 402 of FIG. 4, which an overseer may use to track the precision level (e.g., L1 for level 1) which had been completed for each test. Similarly, in some cases, a data menu template such as shown in FIG. 4 could be implemented to provide additional interfaces and/or tools to assist an overseer in tracking and facilitating experimental studies at one or more remote laboratories. To illustrate, consider FIGS. 10-16, which depict additional interfaces which could be provided by a data menu template such as shown in FIG. 4 and which could assist an overseer in tracking and facilitating experimental studies at one or more remote labs.

Starting with FIG. 10, that figure depicts an interface which might be provided in a case where a data menu template such as shown in FIG. 4 is implemented as a spreadsheet which includes not only the columns shown in FIG. 4, but also additional columns which may be used for purposes such as adding information about tests as or after they take place. In particular, as shown in FIG. 10, these additional columns might include a comments column 1001 which an overseer may use to add additional information about a test, such as that it failed an initial test run, and columns for various tasks which may be used to track the status of those tasks for the relevant test (e.g., Sequel Generated Y/N 1002, which may be used to track whether data from a run had been retrieved using an SQL query, in embodiments where that approach for data capture 209 and transmission was used). FIG. 10 also includes columns 1003-1006 for different machines which may either be tested or used for reference during the testing. In some embodiments, these columns may be set up during preliminary setup 202 in a method such as shown in FIG. 2, with each column heading indicating the serial number (e.g., 11111, 22222, 33333, 44444) of a machine involved in the testing. The individual rows in those columns may then be marked to indicate what the various machines' involvement would be. For example, for methods tests where ALP and Acetaminophen tests were run on machine 22222 with machine 11111 used as a reference and Ferritin and AFP tests run on machine 44444 with machine 33333 used as a reference, marks such as the letter "x" could be added to the first and second rows of the columns for machines 11111 and 22222, and similar marks might be added to the third and fourth rows of the columns for machines 33333 and 44444.

FIG. 11 also presents an interface which may be provided in a case where a data menu template such as shown in FIG. 4 is implemented as a spreadsheet, but FIG. 11 presents an interface which might be accessed by switching to a new sheet rather than by scrolling through columns. In particular, to access the interface of FIG. 11 from the interface of FIG. 4, in some embodiments an overseer might select the sheet label 403 corresponding to the programming log for an instrument on which one or more experimental studies were going to performed. On the interface of FIG. 11 the overseer would be presented with columns that may be used to track the status of, and record relevant data for, activities which would have to take place for an experimental study on a particular instrument to be deemed complete. For example, when programming 705 the rack(s) which would be used for a study, in addition to entering sample IDs into (or instructing an individual at the laboratory where the test would take place to enter the sample IDs into) an interface such as shown in FIG. 6, an overseer could enter the IDs of the sample(s) into a sample IDs column 1101 in the row corresponding to the study in question. The rack and panel columns could similarly filled in as the corresponding information for those columns was input during instrument configuration 204 or post-calibration setup 207.

In addition to the columns where an overseer could record data entered during a screen sharing session to prepare an instrument for testing, the interface of FIG. 11 also includes tracking columns which an overseer could use to indicate if an activity, to the extent applicable for a particular task, had been completed. To illustrate, consider the four tasks listed in FIG. 11, and the information provided in the instrument process 1102 data collection 1103 and timing 1104 column groups for those tasks. For the first task, configuring the instrument (corresponding to the configuring 204 step from the flowchart of FIG. 2), because this configuration does not include gathering any data, or entering data for any specific studies, each of the entries for that task in the instrument process 1102 and data collection 1103 column groups may have default values of NA (i.e., not applicable), and the overseer may not modify those values when the configuration was complete. However, the overseer would enter data into the timing 1104 column group to indicate when and for how long that task was being performed. For the next task, reagent load/cal (corresponding to the loading 205 and calibration 206 steps from the flowchart of FIG. 2), while the instrument process column group would continue to be not applicable, the data review 1105 and raw data 1106 columns of the data collection 1103 column group would be relevant to this task, and could be used by the overseer to track its completion. Specifically, once a calibration report had been generated, the overseer might change the entry in the raw data column 1106 from its default value of N (i.e., not complete) to C (i.e., complete) to show that the raw data from the calibration was available, and once that report had been reviewed and it was confirmed that the calibration had been successful, a similar change could be made to the data review column 1105. The overseer could also use the comments column 1107 to add additional information about the task (e.g., if the instrument initially failed and the task had to be repeated).

In some embodiments, the use of the interface of FIG. 11 for tracking the tasks of completing the precision and linearity studies may be similar. In the instrument process column group 1102, once the pre-calibration setup 207 was complete and the instrument was ready for performance 208 of the tests, the overseer might change the value in the instrument prog column 1108 to Y, to indicate that programming was complete. Similar changes may be made in the in process and complete columns when respectively, the testing had been started and it was finished. The interface of FIG. 11 also includes columns to track activities which may take place after testing for a study was done, but which would need to be finished for the study to be deemed complete. Specifically, in some embodiments, the raw data column 1106 might be used to indicate whether the data from the testing had been captured and was ready for analysis (corresponding to the capture data 209 step from FIG. 2). In some embodiments, the data review column 1105 might be used to specify whether that data had been analyzed (corresponding to step the analysis step 210 from FIG. 2). In some embodiments, the DR column 1109 might be used to specify whether it had been determined that the test(s) succeeded (corresponding to the test passed determination 211 from FIG. 2). In some embodiments, the data capture column 1110 might be used to indicate whether a hard copy of the raw data had been created and was available at the laboratory for use in verifying compliance with the laboratory's testing requirements (corresponding to the print raw data step 212 from FIG. 2), whether the file upload was complete, etc. Finally, in some embodiments, the print summary column 1111 might be used to indicate whether a hard copy of the summary report had been created and was available at the laboratory for use in verifying compliance with the laboratory's testing requirements (corresponding to the print instrument reports step 213 from FIG. 2).

Of course, it should be understood that variations are possible on how an interface such as shown in FIG. 11 might be used to assist with tracking of activities in particular, and/or with overseeing of testing more generally. For example, while the above description explained that an overseer might use the timing columns 1104 of FIG. 11 to record the start time, finish time and duration for various tests, it is possible that, in some cases, one or more of those timing columns 1104 might be omitted, or information described above as being entered by an overseer might be provided automatically. For instance, in some embodiments it is possible that a system implemented based on this disclosure could include functionality which would automatically provide an expected duration for completing a particular test, rather than requiring an overseer to input that information manually. With this information, an overseer who was responsible for tests at multiple locations might be able to know that, once a particular test was started, he or she would be able to spend that test's expected duration setting up or performing other tasks for a different test without interfering with or delaying completion of the study the first test was included in. Other types of variations, such as removal of one or more of the columns shown in FIG. 11 (e.g., removing the duration column and only requiring collection of the date and start and finish times for a test) are also possible and will be immediately apparent to those of ordinary skill in the art in light of this disclosure. Accordingly, the discussion above of using an interface such as shown in FIG. 11 to track the progress of a test should be understood as being illustrative only, and should not be treated as limiting.

Figure 13:
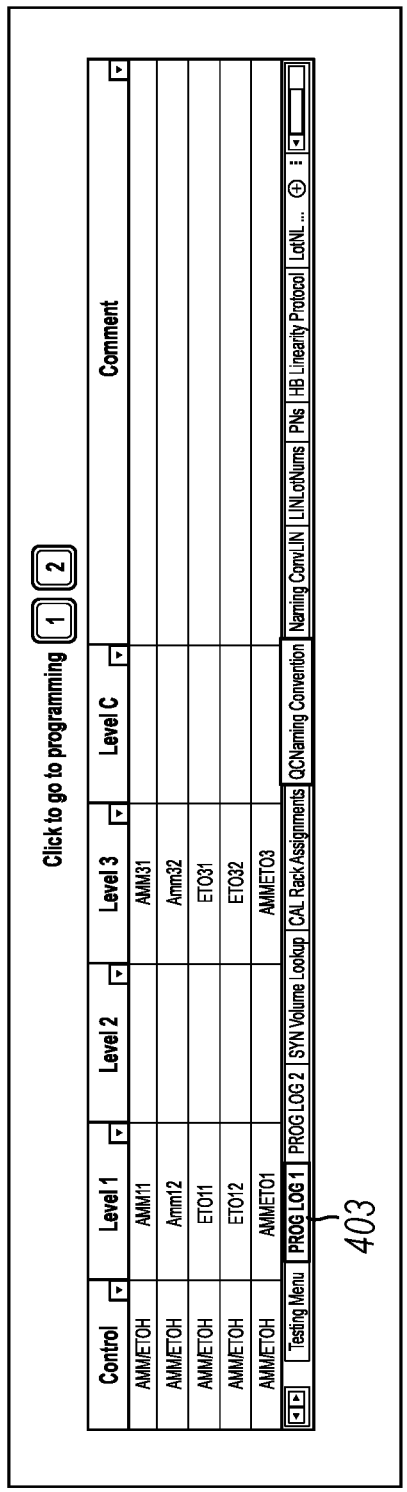
FIG. 13 provides an example embodiment of an interface that could be provided by a tool used by an overseer during experimental studies.
Figure 15:
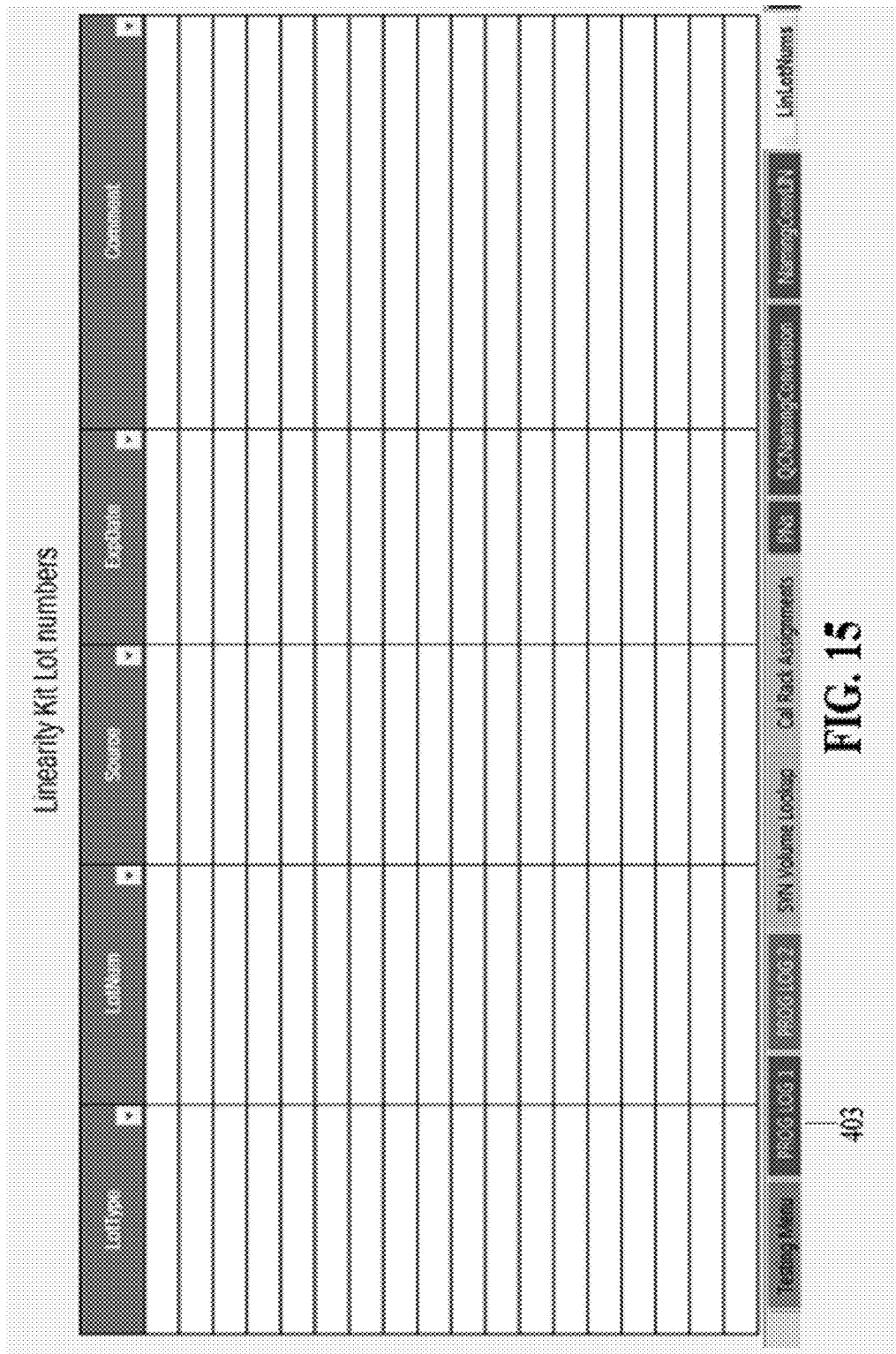
FIG. 15 provides an example embodiment of an interface that could be provided by a tool used by an overseer during experimental studies.

Turning now to FIGS. 12-16, those figures provide further examples of interfaces which, in the exemplary data menu template of FIG. 4, may be implemented as separate sheets which might be accessed through their respective sheet labels. FIG. 12 depicts a sheet which presents predefined rack assignments for calibrators, which, in some embodiments, an overseer might use to instruct an individual at a laboratory where the appropriate calibrators should be loaded into an instrument during the calibration step 206 from FIG. 2. FIG. 13 depicts a sheet which presents naming conventions for quality controls that might, in some embodiments, be used in identifying data generated during a test for purpose of subsequent data analysis 210. For example, to indicate that data was from an ammonia test, a naming convention such as shown in FIG. 13 might start with the characters "AMM," this might be followed with a number to indicate the precision level of the test data ("AMM1" for level 1, and "AMM3" for level 3), and a number of the cup for the test ("AMM11" for a level 1 test in cup 1). FIG. 14 depicts a sheet which presents naming conventions for linearity levels, which, in some embodiments, might be programmed into a laboratory instrument on which a linearity study was to be performed as part of the post-calibration setup 207, and which that instrument might then include in its output to enable the data generated during a test to be properly interpreted by the program used during the analysis 210 of the test's data. FIG. 15 depicts a sheet which, in some embodiments, might also be populated with information that might be used to assist with the analysis of data generated during a test. In particular, FIG. 15 depicts an interface which might be filled in with information regarding kits that might be used during the testing (e.g., this might be obtained, for example, by copying the table shows in FIG. 15 into an email, sending it to the laboratory, and requesting that the laboratory personnel fill it in and email it back) and might subsequently be provided to the software which would perform the analysis 210 of the data generated during the test, and potentially also retained in the template for recordkeeping purposes. FIG. 16 depicts product numbers for reagents, calibrators and other types of consumables for particular tests. This information might, in some embodiments, be used by an overseer during the preliminary setup 202 step of FIG. 2 to identify the products that would need to be available for an experimental study to go forward.

Figure 3:
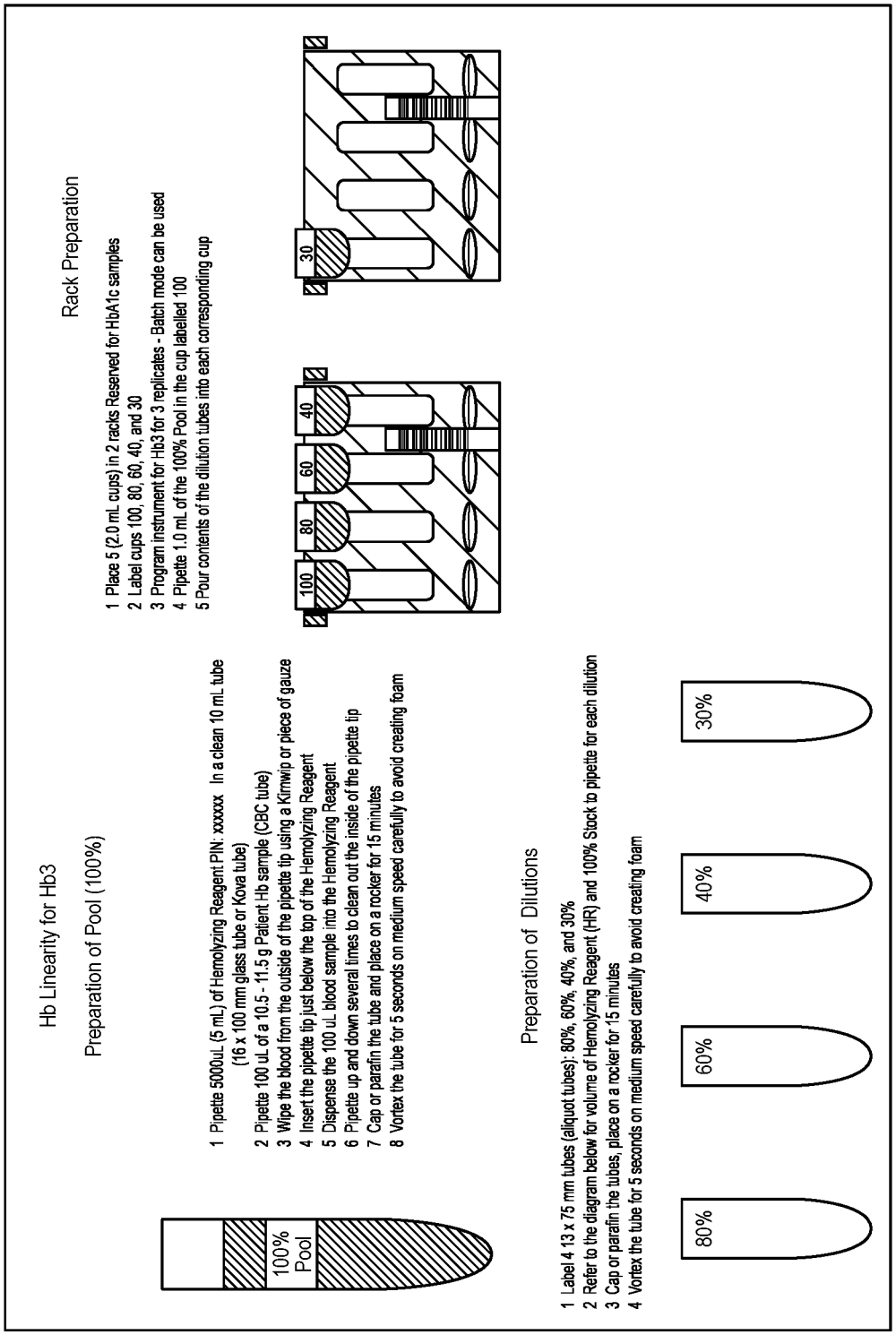
FIG. 3 provides an example embodiment of an instructional chart that could be used to provide assistance to a laboratory.
Figure 18:
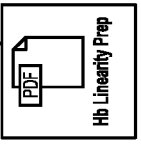
FIG. 18 provides an example embodiment of an interface with information that could be used in sample preparation.

It should be understood that, while FIG. 4 and FIGS. 10-16 depict interfaces which could be provided by a data menu template, it is possible that, in some embodiments, interfaces such as shown in FIGS. 4 and 10-16 or other tools for supporting an overseer, might be provided independently of a data menu template. To illustrate, consider FIG. 17, which depicts a tool that, in some embodiments, might be used to calculate the amount of sample required for a study. This type of tool might, for example, be provided in the form of an application running on a workstation at a network instrument monitoring center 105, which an overseer might execute during the post-calibration setup 207 to assist with determining 703 and preparing 706 the sample container. Similarly, FIG. 18 depicts an interface which, in some embodiments, might be provided by a sample preparation application, and used by an overseer as a reference when assisting an individual at a laboratory with sample preparation 706. Additionally, the interface of FIG. 18 also includes a control 1801 which might, in some embodiments, be used by the overseer to obtain an instructional PDF like that shown in FIG. 9 or FIG. 3 that could be transmitted to the laboratory as a form of further assistance for the individual actually preparing the sample(s) to be used in the test(s). Of course, while FIGS. 17 and 18 were described above as being provided by applications separate from the data menu template of FIG. 4, it is also possible that, in some embodiments, tools such as shown in FIGS. 17 and 18 might be integrated with a data menu template, such as in the form of additional sheets. Accordingly, the discussion above regarding functionality which could be provided by a data menu template or through one or more separate application should be understood as being illustrative only, and should not be treated as limiting.

Variations on what type of supporting infrastructure might be provided beyond simply what functionality is or is not integrated into a data menu template are also possible. For example, as noted above in the discussion of FIG. 11, in some embodiments, an overseer might be required to manually update a data menu template (or other record) as various tasks included in a study take place. This type of manual updating would preferably be included because it could help ensure that the individual overseeing the test(s) was aware of and involved with the status of each of the tests he or she was responsible for. However, in some embodiments, manual tracking might not be required. For instance, in some embodiments an instrument being tested might be programmed to send a status message to the overseer when an activity/milestone had been completed, and software at that location could then use that message to automatically update whatever tool was being used to track status and to provide an alert to the overseer so that he or she would be aware the update had taken place. As an example of another type of variation, in some embodiments, an individual overseeing multiple studies might be provided an option to use have tests displayed by their status (e.g., by filtering and/or sorting tests based on status columns such as described previously) so that he or she might quickly determine the status of each test, and avoid any individual test being inadvertently neglected. Similarly, in cases where there are limits on the length of time which is acceptable between study activities (e.g., when a test requires use of a refrigerated material, in which case the test which uses that material might need to be performed within a set time period of when the material is loaded into the instrument), software running at either the laboratory or the location of the overseer could track the applicable time limits, allow the overseer to sort a list of pending activities by the time remaining for them to take place, and/or might provide alerts when the time during which an activity would have to be performed was in danger of expiring.

Another example of where there might be infrastructure which might be used to support steps such as shown in FIG. 2 is in communication between an overseer and an individual at the location of the instrument being tested. For instance, in some embodiments, all such communication might be performed in the context of the screen sharing session established 203 prior to testing, with comments back and forth being entered in a notes field for a test which might be seen at both the laboratory and the location of the remote overseer simultaneously on those individuals' shared screen as they were typed. Alternatively, in some embodiments multiple channels of communication might be used, including screen sharing sessions, separate audio or video links for voice or video calls, chat sessions, and email or other file transfer mechanism for sending instructional documents to assist with activities which would take place at the laboratory. As yet a further example of variations in the type of infrastructure which might be provided to support a method such as shown in FIG. 2, while the discussion above referred to an overseer being located at a network instrument monitoring center 105, it is entirely possible that such an individual could be located at some alternative location, or that the process of FIG. 2 and its various supporting features could be deployed in one of the environments discussed in the context of FIG. 1 as an alternative to an environment where personnel at a network instrument monitoring center 105 rely on their own local equipment to handle incoming data from remote laboratories. Accordingly, the discussion above of how various infrastructure features could be provided to allow an overseer to simultaneously work on multiple studies at different locations should be understood as being illustrative only, and should not be treated as limiting.

Further variations on, features for, and potential implementations and applications of the inventors' technology will be apparent to, and could be practiced without undue experimentation by, those of ordinary skill in the art in light of this disclosure. Accordingly, neither this document, nor any document which claims the benefit of this document's disclosure, should be treated as being limited to the specific embodiments of the inventor's technology which are described herein.

As used herein, the singular forms "a", "an", and "the" include plural referents unless the context clearly dictates otherwise. The invention has now been described in detail for the purposes of clarity and understanding. However, it will be appreciated that certain changes and modifications may be practice within the scope of the appended claims.

As used herein, a "computer" should be understood to refer to a group of devices (e.g., a device comprising a processor and a memory) capable of storing and executing instructions for performing one or more logical and/or physical operations on data to produce a result. A "computer" may include, for example, a single-core or multi-core microcontroller or microcomputer, a desktop, laptop or tablet computer, a smartphone, a server, or groups of the foregoing devices (e.g., a cluster of servers which are used in combination to perform operations on data for purposes such as redundancy and availability). In the claims, the word "server" should be understood as being a synonym for "computer," and the use of different words should be understood as intended to improve the readability of the claims, and not to imply that a "sever" is not a computer. Similarly, the various adjectives preceding the words "server" and "computer" in the claims are intended to improve readability, and should not be treated as limitations.

As used herein, the term "machine" refers to a device or combination of devices.

As used herein, "means for allowing an overseer to oversee the performance of experimental studies on one or more remotely located laboratory instruments" should be understood as a limitation set forth as a means for performing a specified function as provided for in 35 U.S.C. § 112(f), where the function is "allowing an overseer to oversee the performance of experimental studies on one or more remotely located laboratory instruments," and the corresponding structure is a computer configured to perform an algorithm comprising (i) establishing screen sharing sessions with displays at locations of laboratory instruments on which studies are to be performed; (ii) making interfaces as shown in FIGS. 4 and 10-18 available to an overseer for use in facilitating and tracking the experimental studies; and (iii) storing information entered into those interfaces by the overseer.

As used herein, the term "network" refers to any collection of networks using standard protocols. For example, the term includes a collection of interconnected (public and/or private) networks that are linked together by a set of standard protocols (such as TCP/IP, HTTP, etc.) to form a global, distributed network. The term is also intended to encompass variations that may be made in the future, including changes and additions to existing standard protocols or integration with other media (e.g., television, radio, etc).

As used herein, the term "sample" refers to any biological sample, and the phrase "biological sample" is meant to cover any specimen of biological material which has been isolated from its natural environment, such as the body of an animal or a human being. It can be in solid form such as tissues, bones, ligaments, and the like. It can also be in liquid form such as blood, spinal fluid, and the like.

As used herein, the term "set" refers to a number, group, or combination of zero or more things of similar nature, design, or function.

As used herein, the term "based on" means that something is determined at least in part by the thing that it is indicated as being "based on." To indicate that something must be completely determined based on something else, it would be described as being based "exclusively" on whatever it is completely determined by.

As used herein, modifiers such as "first," "second," and so forth are simply labels used to improve readability, and are not intended to imply any temporal or substantive difference between the items they modify. For example, referring to items as a "first program" and a "second program" in the claims should not be understood to indicate that the "first program" is created first, or that the two programs would necessarily cause different things to happen when executed by a computer. Similarly, when used in the claims, the words "computer" and "server" should be understood as being synonyms, with the different terms used to enhance the readability of the claims and not to imply any physical or functional difference between items referred to using those different terms.

The invention claimed is:

1. A method comprising:
   remotely facilitating setup and monitoring performance of experimental studies associated with laboratory instruments, by performing acts comprising, for a subject laboratory instrument:
   a) transmitting setup data to a location of the subject laboratory instrument on which a requested study comprising one or more tests is to be performed;
   b) updating a set of one or more study progress values for the subject laboratory instrument indicating the requested study is either complete or in progress; and
   c) updating a set of one or more data collection progress values for the subject laboratory instrument indicating data for the requested study has been captured or reviewed or printed.

2. The method of claim 1, wherein:
   a) the method comprises a single individual at a location remote from both a first laboratory and a second laboratory performing the steps of clauses (a)-(c) of claim 1 a first time with a first laboratory instrument at the first laboratory as the subject laboratory instrument, and a second time with a second laboratory instruct at the second laboratory as the subject laboratory instrument;
   b) at least one of the steps from the first time the steps of clauses (a)-(c) of claim 1 are performed is completed before any of the steps from the second time the steps of clauses (a)-(c) of claim 1 are performed is completed; and
   c) at least one of the steps from the second time the steps of clauses (a)-(c) of claim 1 are performed is completed before all of the steps from the first time the steps of clauses (a)-(c) are performed is completed.

3. The method of claim 2, wherein the set of one or more study progress values and the set of one or more data collection progress values for both the first time the steps of clauses (a)-(c) of claim 1 are performed and the second time the steps of clauses (a)-(c) of claim 1 are performed are stored in a data structure, wherein the data structure comprises a field for each value which is updated during performance of the steps of clauses (a)-(c) of claim 1.

4. The method of claim 3, wherein the data structure is a spreadsheet comprising a first sheet and a second sheet, wherein:
   a) the first sheet comprises data for the first laboratory instrument, wherein the fields for the values which are updated during updating of the set of one or more study progress values and updating of the set of one or more data collection progress values the first time the steps of clauses (a)-(c) of claim 1 are performed are comprised by the first sheet; and
   b) the second sheet comprises data for the second laboratory instrument, wherein the fields for the values which are updated during updating of the set of one or more study progress values and updating of the set of one or more data collection progress values the second time the steps of clauses (a)-(c) of claim 1 are performed are comprised by the second sheet.

5. The method of claim 4, wherein:
   a) the requested study from the first time the steps of clauses (a)-(c) of claim 1 are performed and the requested study from the second time the steps of clauses (a)-(c) of claim 1 are performed are both comprised by an overall concurrent study set;
   b) the spreadsheet comprises a third sheet comprising fields for each test comprised by the overall concurrent study set; and
   c) the method comprises, for each test comprised by the overall concurrent study set, after receiving information indicating that a precision level selected from a group of predefined precision levels has been completed, updating the third sheet to indicate completion of that precision level for that test.

6. The method of claim 5, wherein the method comprises:
   a) for each test comprised by the overall concurrent study set, adding a label for that test to the third sheet;
   b) editing the first sheet to include:
      i) a label for a task of configuring the subject instrument from the first time the steps of clauses (a)-(c) of claim 1 are performed; and
      ii) a label for a task of loading and calibrating the subject instrument from the first time the steps of clauses (a)-(c) of claim 1 are performed;

c) editing the second sheet to include:
  i) a label for a task of configuring the subject instrument from the second time the steps of clauses (a)-(c) of claim 1 are performed; and
  ii) a label for a task of loading and calibrating the subject instrument from the second time the steps of clauses (a)-(c) of claim 1 are performed.

7. The method of claim 4, wherein:
a) the method comprises updating a set of one or more instrument programming values for the subject laboratory instrument by performing steps comprising:
  i) updating the set of one or more instrument programming values to include each rack with at least one sample for the requested study; and
  ii) updating the set of one or more instrument programming values to include an identifier for each sample for the requested study;
b) when the set of one or more instrument programming values is updated for the subject laboratory instrument, it is updated in the sheet in the spreadsheet which comprises the fields for values which are updated when the set of one or more data collection progress values for the subject laboratory instrument is updated; and
c) when the steps of clauses (a)-(c) of claim 1 are performed the steps of clause (a) is performed.

8. The method of claim 1, wherein:
a) transmitting the setup data is performed after calibration of the subject laboratory instrument;
b) the setup data comprises, for each of the one or more tests comprised by the requested study:
  i) an identification of that test; and
  ii) an identification of a number of replicates for that test;
c) the set of one or more study progress values for the subject laboratory instrument are updated by performing steps comprising:
  i) after receiving information indicating the subject laboratory instrument has been programmed to perform the one or more tests comprised by the requested study, updating the set of one or more study progress values to indicate that programming the subject laboratory instrument for that study is complete;
  ii) after receiving information indicating a test from the requested study has been initiated, updating the set of one or more study progress values to indicate that the requested study is in process;
  iii) after receiving information indicating that each of the one or more tests comprised by the requested study is complete, updating the set of one or more study progress values to indicate that the requested study is complete;
c) the set of one or more data collection progress values are updated by performing steps comprising:
  i) after the one or more tests comprised by the requested study have been completed and data generated by those tests is available for analysis, updating the set of one or more data collection progress values to indicate that raw data for the requested study has been captured;
  ii) after the data generated by the one or more tests comprised by the requested study has been analyzed, updating the set of one or more data collection progress values to indicate that the data for the requested study has been reviewed;
  iii) after each of the one or more tests comprised by the requested study has been successfully completed and a hard copy of the data generated by the successful tests has been created and stored at the location of the subject laboratory instrument, updating the set of one or more data collection progress values to indicate that the data for the requested study has been captured; and
  iv) after each of the one or more tests comprised by the requested study has been successfully completed and a hard copy of a summary report generated based on the data generated by the successful tests has been created and stored at the location of the subject laboratory instrument, updating the set of one or more data collection progress values to indicate that the summary for the requested study has been printed.

9. A machine comprising a server, wherein the server is configured with instructions operable to, when executed, allow an overseer to perform the method of claim 1.

10. A computer program product comprising a computer readable medium storing instructions for allowing an overseer to perform the method of claim 1.

* * * * *